United States Patent
Piper, Sr. et al.

(10) Patent No.: US 9,183,714 B2
(45) Date of Patent: *Nov. 10, 2015

(54) ENTRANCE SECURITY SYSTEM

(71) Applicants: Douglas E. Piper, Sr., Greenville, SC (US); Thomas E. Browning, Jr., Belmont, NH (US); Mary Hester Owens, Simpsonville, SC (US); Clifford Leroy DeYoung, Woodruff, SC (US); Sam Snead Shasteen, Greenville, SC (US); Mark C. Phillips, Woodruff, SC (US)

(72) Inventors: Douglas E. Piper, Sr., Greenville, SC (US); Thomas E. Browning, Jr., Belmont, NH (US); Mary Hester Owens, Simpsonville, SC (US); Clifford Leroy DeYoung, Woodruff, SC (US); Sam Snead Shasteen, Greenville, SC (US); Mark C. Phillips, Woodruff, SC (US)

( * ) Notice: Subject to any disclaimer, the term of this patent is extended or adjusted under 35 U.S.C. 154(b) by 387 days.

This patent is subject to a terminal disclaimer.

(21) Appl. No.: 13/653,704

(22) Filed: Oct. 17, 2012

(65) Prior Publication Data

US 2014/0139337 A1    May 22, 2014

(51) Int. Cl.
G08B 13/00    (2006.01)
G08B 13/186   (2006.01)
A61B 1/00     (2006.01)
H01L 21/00    (2006.01)
G08B 13/12    (2006.01)

(52) U.S. Cl.
CPC .............. *G08B 13/186* (2013.01); *A61B 1/00* (2013.01); *G08B 13/124* (2013.01); *H01L 21/00* (2013.01)

(58) Field of Classification Search
CPC .................................. H01L 21/00; A61B 1/00
USPC .............. 340/541, 555, 540; 250/216, 227.14
See application file for complete search history.

(56) References Cited

U.S. PATENT DOCUMENTS

| | | |
|---|---|---|
| 4,369,437 A | 1/1983 | Thompson, Jr. et al. |
| 4,447,123 A | 5/1984 | Page et al. |
| 4,777,476 A | 10/1988 | Dank |
| 4,814,562 A | 3/1989 | Langston |
| 4,829,286 A | 5/1989 | Zvi |
| 5,049,855 A | 9/1991 | Slemon et al. |
| 5,055,827 A | 10/1991 | Philipp |
| 5,434,557 A | 7/1995 | Alizi |
| 5,592,149 A | 1/1997 | Alizi |
| 5,594,239 A | 1/1997 | Lessing |
| 5,790,285 A | 8/1998 | Mock |
| 6,002,501 A | 12/1999 | Smith et al. |
| 6,980,108 B1 | 12/2005 | Gebbia et al. |
| 7,068,166 B2 | 6/2006 | Shibata et al. |
| 7,123,785 B2 | 10/2006 | Iffergan |
| 7,782,196 B2 * | 8/2010 | Piper et al. ............... 340/541 |
| 8,514,076 B2 * | 8/2013 | Piper et al. ............... 340/555 |
| 2004/0233054 A1 | 11/2004 | Neff et al. |
| 2006/0196238 A1 | 9/2006 | Avni |

* cited by examiner

*Primary Examiner* — Shirley Lu
(74) *Attorney, Agent, or Firm* — Southeast IP Group, LLC.; Thomas L. Moses

(57) ABSTRACT

An entrance denial security system comprises an entrance barrier closing an entrance into a secured area having a plurality of structural tubular elements with hollow cores forming a rigid integral barrier. At least one optical fiber sensor line is laced through the hollow cores of the structural elements for detecting a fault condition signifying an unauthorized intrusion attempt. A processor in communication with the fiber sensor line generates a fault signal in response to a fault signal level. A communication device operatively associated with the processor communicates the fault signal and an alarm. The system also includes a plurality of tubular elements lying a common plane and the sensor line is routed through the tubular elements. In one instance, the tubular elements are PVC pipe.

37 Claims, 24 Drawing Sheets

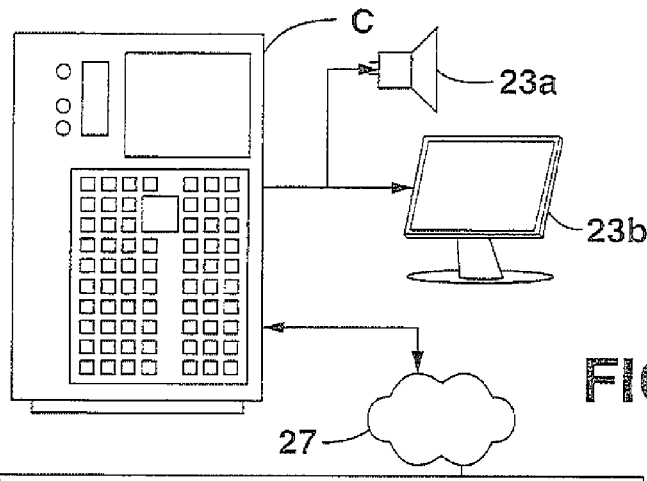
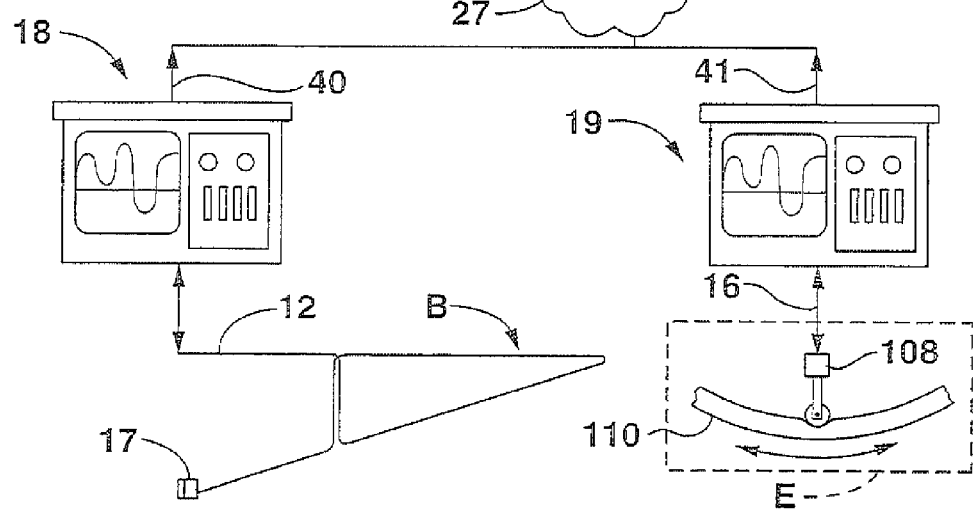
FIG. 2
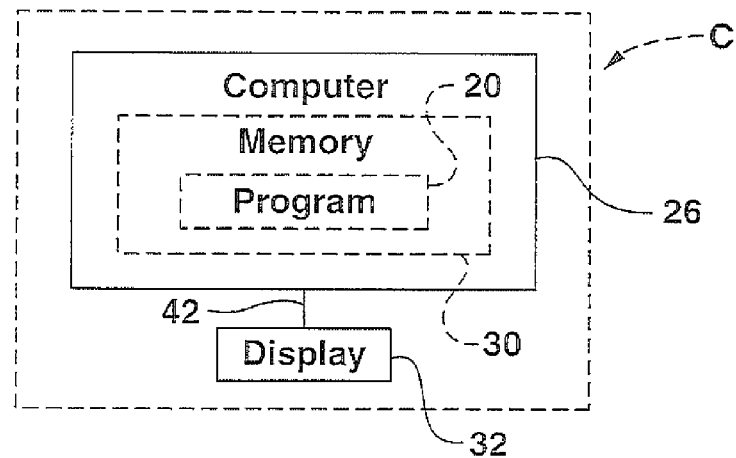
FIG. 3

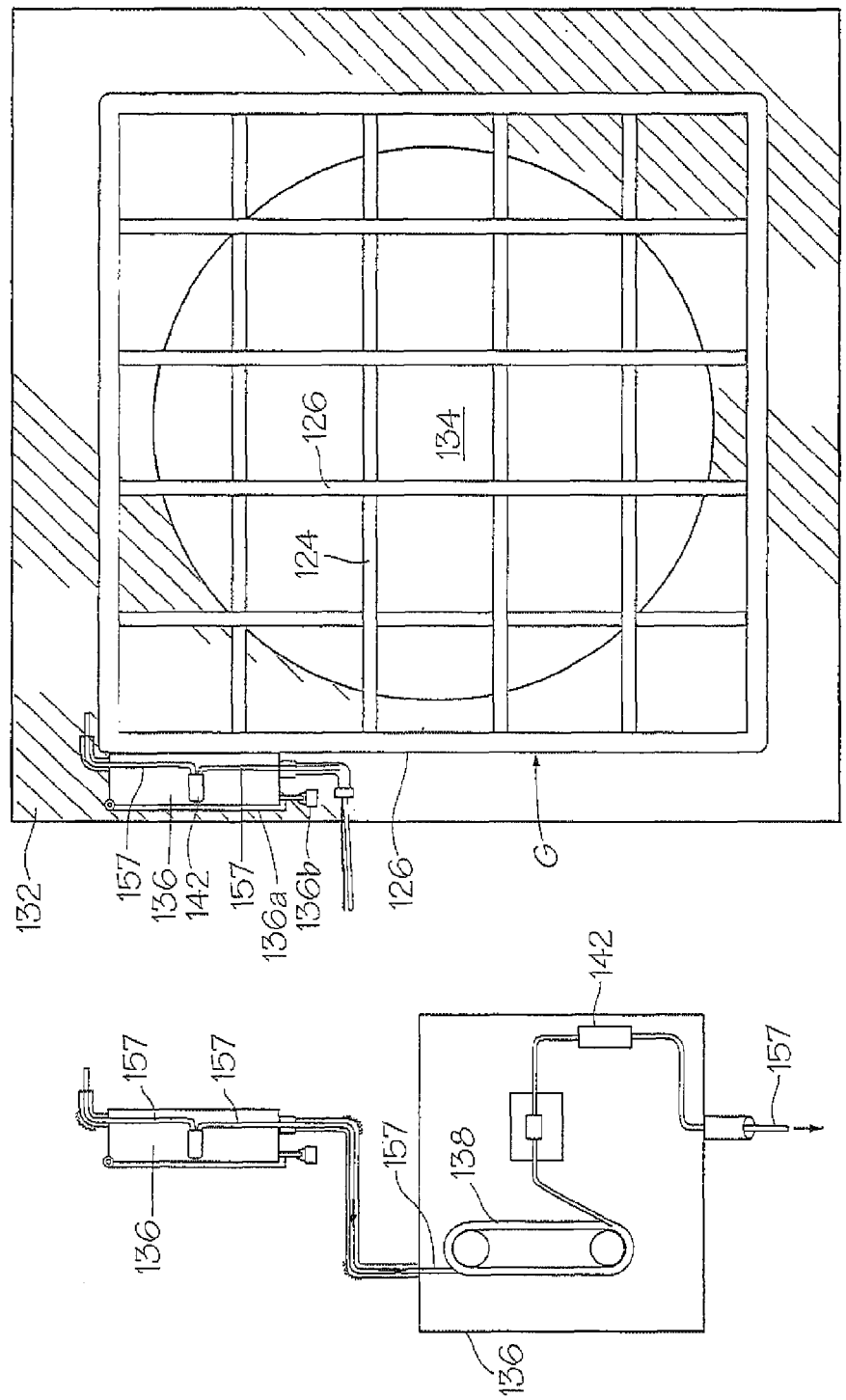

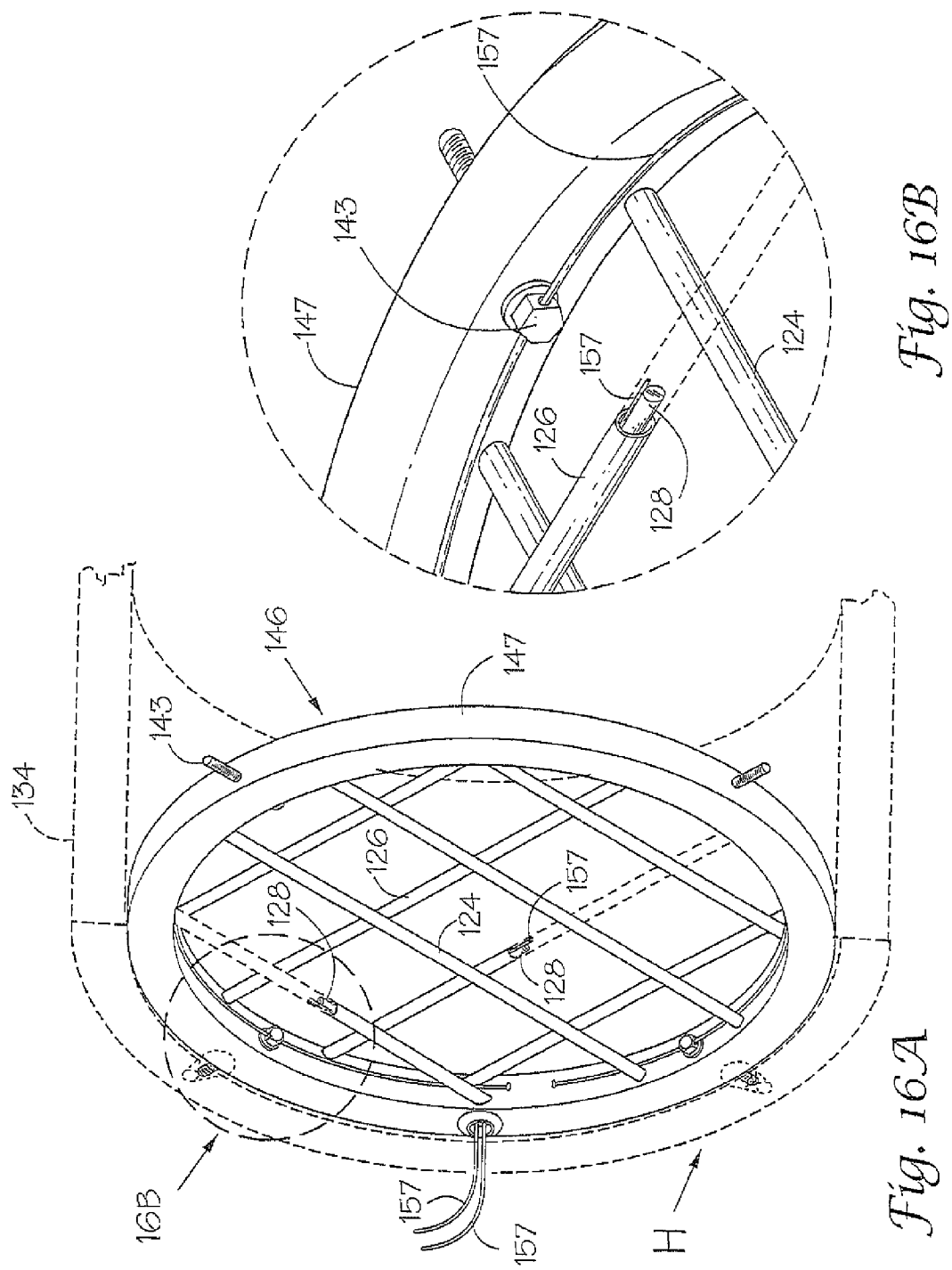

ENTRANCE SECURITY SYSTEM

CROSS REFERENCE TO RELATED APPLICATIONS

This application claims priority from U.S. provisional application no. 60/456,687, filed Mar. 15, 2003, entitled "Fiber Optic Security System For Sensing the Intrusion Of Secured Locations," U.S. non-provisional application Ser. No. 10/429,602, filed May 5, 2003, entitled "Fiber Optic Security System For Sensing Intrusion Of Secured Locations;" PCT application no. PCT/US2004/013494, filed May 3, 2004, entitled "Fiber Optic Security System For Sensing The Intrusion Of Secured Locations;" U.S. provisional application No. 60/626,197, filed Nov. 9, 2004, entitled "Vehicle Denial Security System;" U.S. non-provisional application Ser. No. 11/083,038, filed Mar. 17, 2005, entitled "Apparatus And Method For A Computerized Fiber Optic Security System;" now U.S. Pat. No. 7,800,047 issued Sep. 21, 2010; U.S. provisional application No. 60/673,699, filed Apr. 21, 2005, entitled Secure Above Ground Fiber Optic Data Transmission Cable;" PCT application no. PCT/US2005/040079, filed Nov. 4, 2005, entitled Vehicle Denial Security System;" PCT application no. PCT/US2005/040080, filed Nov. 5, 2005, entitled "Apparatus and Method for a Computerized Fiber Optic Security System;" PCT application no. PCT/US2006/014601, filed Apr. 19, 2006, entitled "Secure Transmission Cable;" U.S. non-provisional application Ser. No. 10/555,534 filed May 10, 2006 entitled "Fiber Optic Security System For Sensing The Intrusion of Secured Locations, now U.S. Pat. No. 7,402,790 B2 issued Jul. 22, 2008; U.S. non-provisional application Ser. No. 11/655,433, filed Jan. 19, 2007, entitled "Entrance Security System," now U.S. Pat. No. 7,782,196 B2 issued Aug. 24, 2010; and U.S. non-provisional application Ser. No. 11/890,450, filed Aug. 6, 2007, entitled "Double-End Fiber Optic Security System For Sensing Intrusions," now U.S. Pat. No. 7,852,213 B2 issued Dec. 14, 2010; and U.S. non-provisional application Ser. No. 12/448,988 filed Jan. 22, 2008 entitled "Entrance Security System," now pending; U.S. non-provisional application Ser. No. 12/321,644 filed Jan. 23, 2009, entitled "Fiber Optic Security System for Sensing The Intrusion of Secured Locations," now U.S. Pat. No. 7,956,316 B2 issued Jun. 7, 2011 each of the above identified applications/patents is incorporated by reference.

BACKGROUND OF THE INVENTION

This invention relates to an entry denial security system for denying entry of a vehicle or person into a secured area and/or detecting an attempt to penetrate a barrier closing an entrance into the secured area.

With the increase in terrorism in the United States and the rest of the world, the need for an effective security system to detect and/or prevent the unauthorized entry of a vehicle and/or individual from breaking through a barrier closing an entrance into a secured area is a problem to which considerable attention needs to be given. In particular, an objective of this invention is to provide an entrance security system which detects an unauthorized opening or break through of an entrance barrier closing an entrance of the secured area.

SUMMARY OF THE INVENTION

The above objectives are accomplished according to the present invention by providing a security system for detecting an unauthorized activity and attempt to enter through an entrance of a secured area and determining the nature and location of the activity. The security system comprises an entrance barrier closing the entrance, including a plurality of hollow structural elements forming an integral barrier structure such as an entrance gate (or fixed barrier). Preferably, fiber optic sensor lines sense a first fault condition representing an unauthorized attempt to open the gate, and a severance of a structural element of the barrier. Advantageously, a longitudinal reinforcing member in the form of a solid stainless steel rod may be enclosed in the tubular elements along with the sensor lines which must be severed before intrusion. This delays intrusion after the sensor line is severed and an alarm signal generated so that ample time is provided for guard personnel to arrive before intrusion. At least one fiber optic scanning unit scans the optical sensor lines and receives scan signals in the optical sensor lines. A system computer is provided for receiving and processing the scan signals in real-time representing the condition of the optical sensor lines and generating a real-time fault signal in response to a predetermined reflection in one or more of the scan signals indicating the unauthorized activity has occurred. A communication device communicates notice of the fault signal to security personnel. Advantageously, the processing of the scan signals includes comparing the real-time scan signals to pre-established baseline scan signal which is characteristic of the first and second sensor lines, respectively, in an undisturbed, secure state.

The barrier is composed of hollow structural elements having hollow cores, and the first optical sensor line is laced through the hollow cores of the structural elements. When the barrier is an entrance gate, the gate is moveable and has an open position allowing entry and a closed position preventing entry. In this case, the system includes a sensor unit disposed relative to the entrance gate to detect movement of the gate toward the open or removed position and generate a fault signal. The sensor unit may include a reciprocating sensor actuator having a deactivated position and an activated position. The sensor actuator engages the second sensor fiber upon the unauthorized movement of the entrance gate causing the sensor actuator to move to the activated position and the fault signal to be generated.

In another aspect of the invention, a method of preventing an unauthorized entry through an entrance into a secured area comprises providing an optical fiber sensor line laced through a plurality of structural elements forming a barrier closing the entrance, and reinforcing the tubular elements with a solid metal rod that delays cut through of the tubular elements until after the sensor line is cut and a fault signal generated. The method includes generating real-time scan signals in the fiber sensor line representing the current state of the fiber sensor line; processing the scan signal to establish a baseline signal from the sensor line representing an undisturbed state of the optical fiber sensor line; and comparing the scan signals to the baseline signal. A fault signal is generated in response to receiving a scan signal having a predetermined deviation from the baseline signal. The method includes processing the fault signal to establish a nature and location of a fault condition occurring in the barrier at the entrance using a stored set of computer readable signature fault conditions; and alerting personnel of the fault condition.

DESCRIPTION OF THE DRAWINGS

The construction designed to carry out the invention will hereinafter be described, together with other features thereof.

The invention will be more readily understood from a reading of the following specification and by reference to the accompanying drawings forming an element thereof, wherein an example of the invention is shown and wherein:

FIGS. 2 and 3 are schematic diagrams illustrating a computerized security interface component for an entrance security system according to the invention;

FIG. 14A is a front elevation of a barrier grate covering the entrance of a culvert according to the invention;

FIG. 14B is a schematic diagram of a service box containing a reserve loop which allows the grate to be removed from its frame, and a door sensor for detecting opening of the service box door;

FIG. 16A is an alternate embodiment of a grate barrier mounted inside the diameter of a culvert according to the invention;

FIG. 16B is an enlargement view showing attachment and securing of the grate by means of bolts and tubular elements laced with fiber optic sensor line;

DESCRIPTION OF A PREFERRED EMBODIMENT

Figure 1:
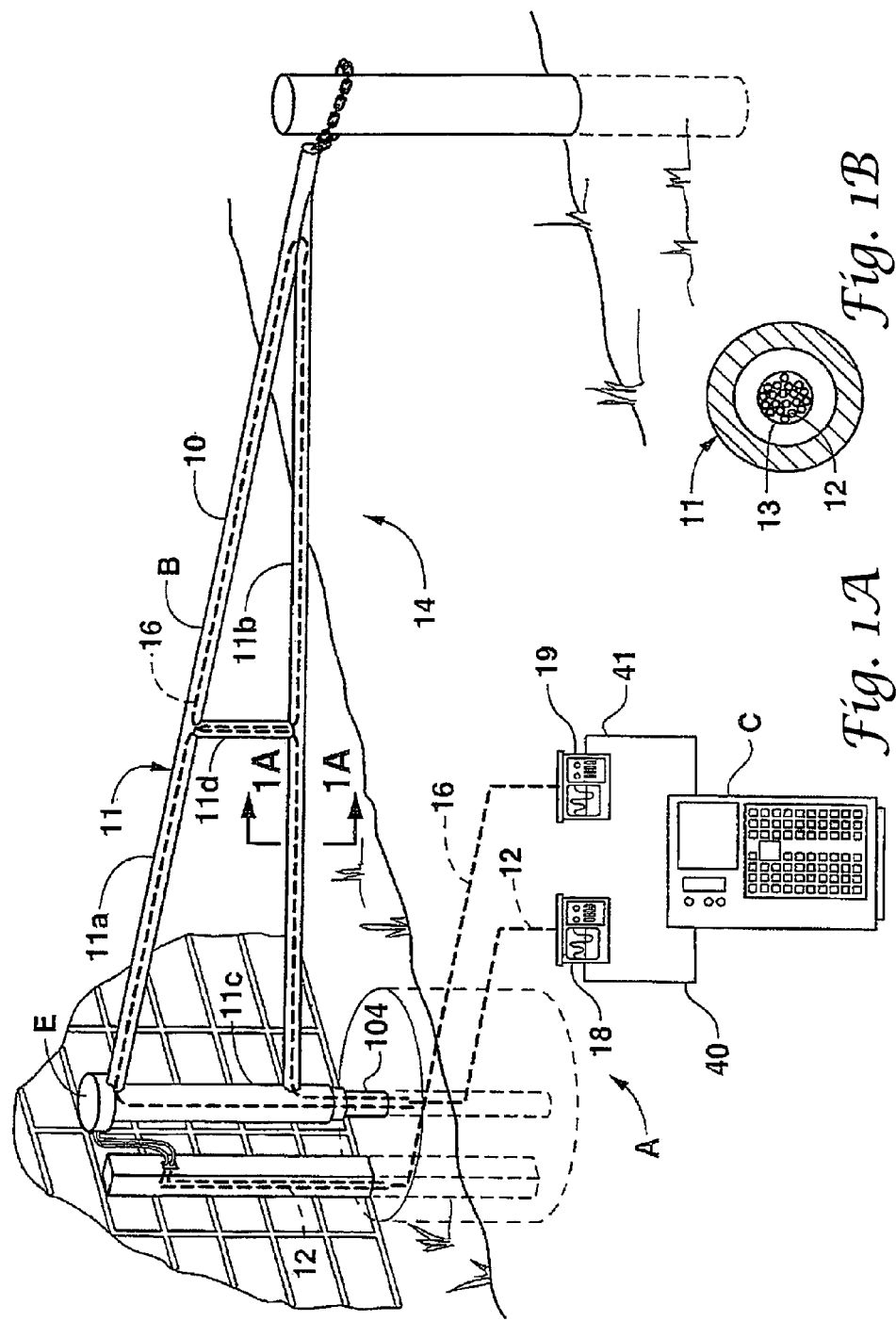
FIG. 1A is a schematic diagram illustrating one embodiment of a gate assembly for an entrance security system according to the invention.
FIG. 1B is a sectional view taken along line 1A-1A of FIG. 1.

The present invention is now described more fully herein with reference to the drawings in which the preferred embodiment of the invention is shown. This invention may, however, embody other forms and should not be construed as limited to the embodiment set forth herein. Rather, these embodiments are provided so that this disclosure will be thorough and complete and will fully convey the scope of the invention to those skilled in the art.

The detailed description of some of the components that follow may be presented in terms of steps of methods or in program procedures executed on a computer or network of computers. These procedural descriptions are representations used by those skilled in the art to most effectively convey the substance of their work to others skilled in the art. These procedures herein described are generally a self-consistent sequence of steps leading to a desired result. These steps require physical manipulations of physical quantities such as electrical or optical signals capable of being stored, transferred, combined, compared, or otherwise manipulated. A computer readable medium can be included that is designed to perform a specific task or tasks. Actual computer or executable code or computer readable code may not be contained within one file or one storage medium but may span several computers or storage mediums. The terms "computer," "processor," and "server" may be hardware, software, or combination of hardware and software that provides the functionality described herein, and may be used interchangeably.

Certain aspects of the present invention are described with reference to flowchart illustrations of methods, apparatus ("systems"), or computer program products according to the invention. It will be understood that each block of a flowchart illustration may be implemented by a set of computer readable instructions or code. These computer readable instructions may be loaded onto a general purpose computer, special purpose computer, or other programmable data processor or processing apparatus to produce a machine such that the instructions will execute on a computer or other data processing apparatus to create a means for implementing the functions specified in the flowchart block or blocks. Accordingly, elements of the flowchart support combinations of means for performing the special functions, combination of steps for performing the specified functions and program instruction means for performing the specified functions. It will be understood that each block of the flowchart illustrations can be implemented by special purpose hardware based computer systems that perform the specified functions, or steps, or combinations of special purpose hardware or computer instructions.

Referring now to the drawings, the invention will now be described in more detail. As can best be seen in FIGS. 1 and 2, an entrance security system, designated generally as A, is schematically illustrated. The security system includes a barrier assembly component, designated generally as B, serving to prevent passage through an entrance of a secured area; and a security interface component, designated generally as C. Barrier assembly B prevents passage of a vehicle, individual, or other object, and generates a fault signal if attempt is made to compromise the barrier closing an entrance 14 into a secured area. The illustrated embodiment, barrier component includes a removable gate 10 closing an entrance into a secured area. The gate includes a plurality of elongated, hollow structural elements 11 arranged in an intersecting pattern forming a triangular gate. The gate structure includes a horizontal element 11 *a*, an intersecting element 11 *b*, a base element 11 *c*, and an intermediate element 11*d*. It is to be understood, of course, that the barrier component may be a movable gate, a fixed barrier, or any other barrier structure closing an entrance, and may be formed in a grid pattern of parallel cross elements, a pattern of interesting or inclined elements, and other arrangements servicing as a barricade to entrance of a secured area. For the purpose that will become apparent hereinafter, structural elements 11 include hollow cores.

A fiber optic sensor line 12 is laced through the hollow cores of hollow elements 11 forming the barrier component, as illustrated in FIG. 1. The fiber optic sensor line enters the gate from the 'left' side. It enters the structure of the gate and is 'laced' through each structural 11 *a*-11 *d* component of the gate assembly. Any attempt to cut the center of the gate, or a supporting pivot post 104 will result in a cutting of the fiber. The sensor line is connected to a scanning unit 18 on one end and to a terminal device 15 on its terminal end. The terminal end of the cable need not be physically or electrically connected to the OTDR. The scanning unit scans the sensor line and receives back a scan signal 40. Any suitable scanning unit, such as an optical time domain reflectometer (OTDR) may be used.

A sensor unit E is secured to the top of gate post 104 for sensing the opening of gate 10 in a manner to be described in more detail hereinafter. Sensor unit E includes an optical fiber sensor line 16 connected to an OTDR 19. A line scan signal 41 is output from OTDR 19 representing the current condition of sensor line 16.

In the illustrated embodiment, security interface component C processes scan signals 40,41 for detecting a prescribed signal attenuation and for determining the nature of an intrusion attempt and identifies the barrier and entrance involved. Fiber optic cable 12 is used to sense opening of the barrier gate. Line scan signal 40 is received by the security interface system and processed to determine if an unauthorized gate movement has occurred. Fiber sensor line 16 is used to detect an attempt to sever, or severance, of a structural element 11 in barrier B. Line scan signal 41 is processed according to established signal characteristics to determine a break or attempted break in the line. Thus, the product provides the capability to monitor a gate at a remote entrance and provide a status (open or closed) and an assessment of any attempt to open the gate, or cut the gate intermediate its ends.

As can best be seen in FIG. 2, security interface component C includes a computer 26 having a computer program 28 containing a set of operating instructions embodied in a computer readable code residing in a memory 30 of the computer. The computer is connected to a display 32 or other communicating device for communicating the occurrence of a fault signal 42 to an operator of the system.

Figure 4:
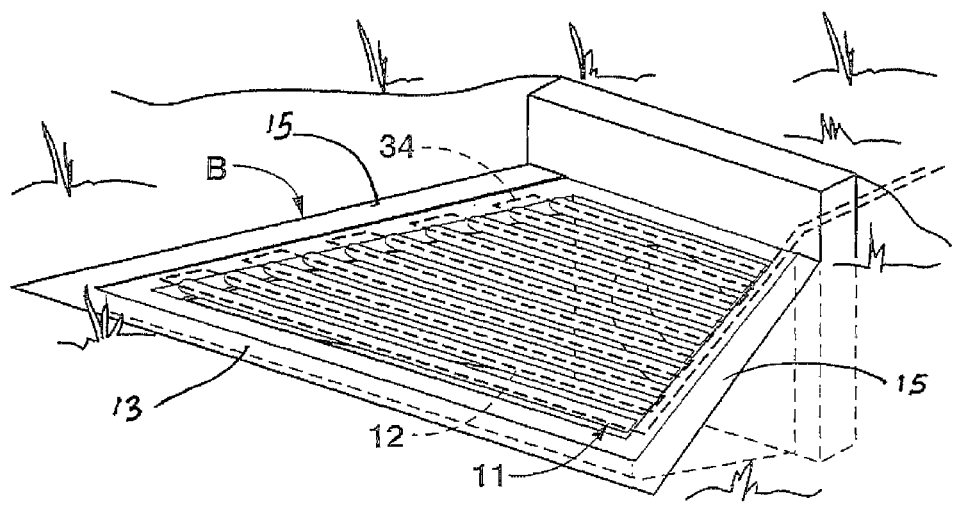
FIG. 4 is a perspective view of a barrier covering the entrance of a culvert having access to a secured area wherein a sensor line is laced through tubular grid elements of the barrier according to the invention.
Figure 5:
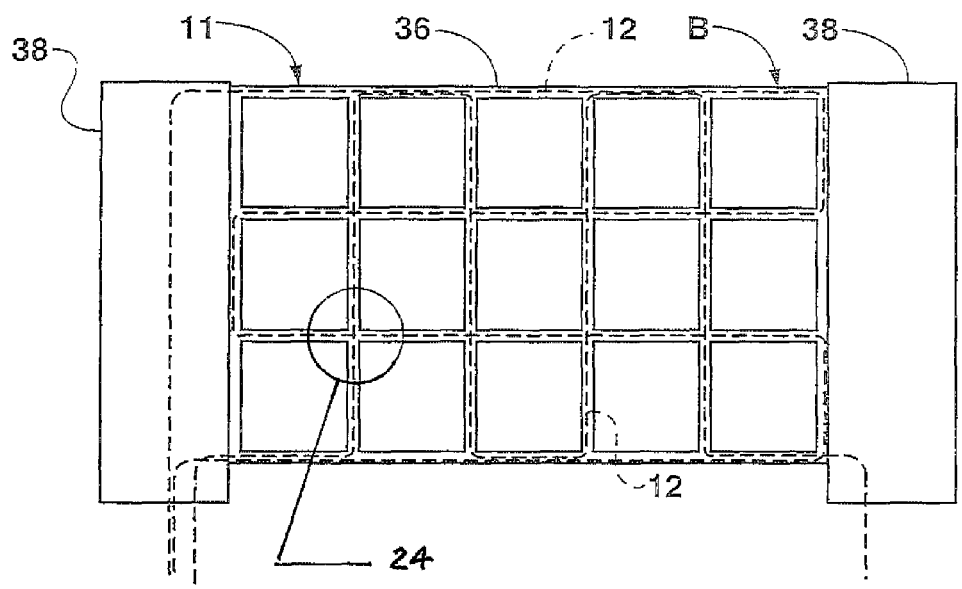
FIG. 5 is a perspective view of another embodiment of an entrance barrier in the form of an entrance gate providing access to a secured area wherein a fiber optic sensor line is laced through the hollow grid elements of the gate.

In the event the line is severed, or the gate is impacted, a fault signal 42 will be generated. As used herein, "fault condition" means a condition in which a structural element 11 of gate 10 has been cut or broken through by a vehicle, or individual, and/or encountered material damage, as distinguished from accidental damage. Fault condition also means an unauthorized opening of the barrier gate to a prescribed open position. While the security system is illustrated as combining the OTDR system 18, 19, other applications may only require one. For example, FIG. 4 illustrates barrier component B in the form of a fixed barrier 34 closing an entrance to a culvert leading to a secured area. The grate barrier includes a series of parallel structural elements 11 laced with one or more sensor lines 12 connected to individual scanning units. Transverse structural members 13 and longitudinal members 15 hold the tubular elements in spaced alignment and transversely fixed. FIG. 5 illustrates barrier component B in the form of a gate 36 (moveable), or a grate barrier (fixed), having structural elements 11 arranged in an intersection grid pattern with one or more sensor lines 12 laced through the grid. The gate or grate barrier closes an entrance through walls or fencing 38. For example, if the barrier is a fixed grate that is generally unmovable, only system 18 may be needed.

The interface security system is computerized and initially must establish a base line signal D for the scan signals 40 coming from the laced gate sensor line 12, and a separate base line signal D for scan signals 41 coming from the sensor unit E. Since the procedure for establishing the base line scan signal is the same, only the procedure for establishing the base line signal for laced sensor line 12 will now be described, it being understood that the procedure for establishing the base line for scan signals 41 is the same.

OTDR 18 continuously scans the optical sensor line within gate assembly B and communicates scan signals 40 in the line to security interface component C, as will be explained more fully below. Computer 26 is programmed to compare the scan signals to a baseline signal D to determine whether predetermined signal deviation representing a fault condition has occurred. In the event the fault condition is detected, fault signal 42 is generated by the interface component along with a computation of the type of fault and location of the fault condition at entrance 12. For example, display 32 may include a map of the area depicting the location of the entrance and fault condition on the map.

Conventional input devices, such as a keyboard or mouse, may be provided for operating computer 26. Other means of displaying the OTDR signal may also be used.

Figure 6:
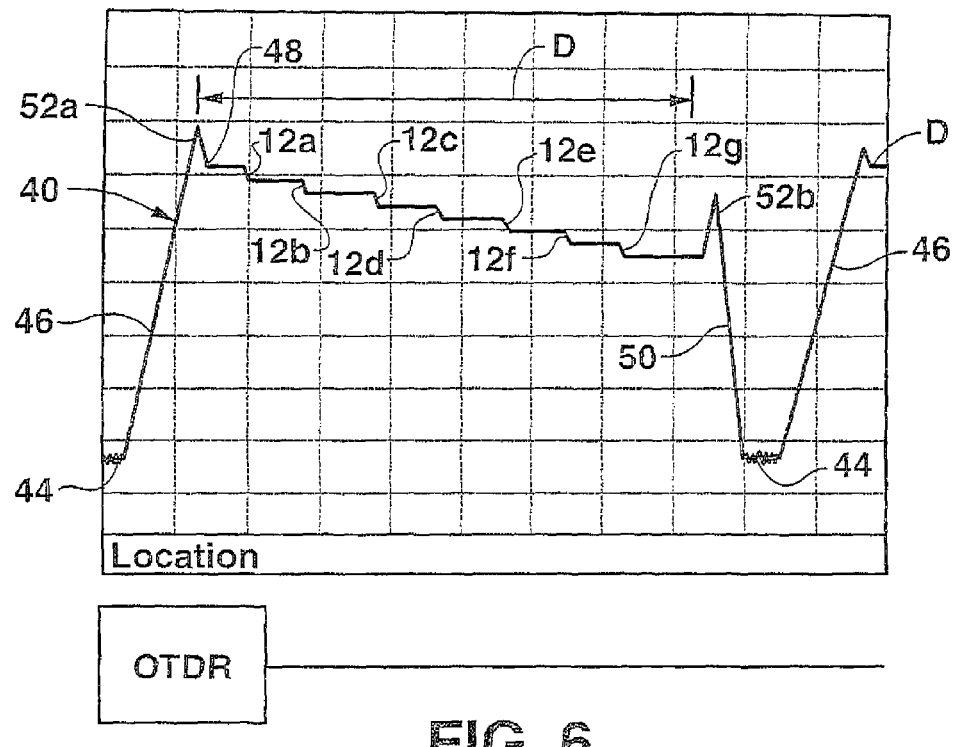
FIG. 6 is a graphic display of the OTDR signal When the vehicle denial security is in a normal, undisturbed condition.

Computer 26 continuously monitors scan signals 40 produced by OTDR 18 when scanning the fiber optic cable. When the computer is first turned on, the computer acquires baseline signal D from the OTDR, as can best be seen in FIG. 6. The baseline represents the status of the fiber optic cable being monitored at a normal, undisturbed state. For example, while initially scanning the line the scan signal will likely include some noise attenuations at 44, followed by a launch signal 46 in the scan. A launch is created by a significant attenuation or spike in the scan to a normalized level. The normalized level at 48 is the beginning of baseline signal D. The system continues to read the baseline until a drop occurs at 50. The drop indicates the end of sensor line 12 being scanned. After the drop, noise 44 again will be recorded by the OTDR. The computer system will then ignore small peaks 52a and 52b at the beginning and at the end of the baseline signal which is merely reflections of the launch and the drop. Baseline signal D established for the security application being made will be compared to all future scans of the fiber optic line to determine if a fault condition has occurred.

During scanning, computer 26 continuously receives scan signals 40 representing scans of fiber optic cable 12 from OTDR 18. A cable being monitored will have a characteristic baseline signal depending on the security application being made and security configuration. A straight cable extending perfectly vertical from the OTDR will be one of the few instances that no attenuations will be found in the baseline. As illustrated in FIG. 1A, fiber optic sensor line 12 will likely have seven characteristic bends when laced through the hollow structural elements of barrier gate B. The bends will likely produce seven distinctive attenuations at 12a through 12g. Each attenuation represents one of the bends in the lines at the intersections of the structural elements. With each repetitive scan, the computer system compares the scan signal to the baseline signal to see if any signal deviations and attenuations are detected. If a signal deviation is detected, the computer analyzes the deviation signal to determine what type of fault has occurred, as well as the specific location of the fault. If the scan attenuation matches a baseline attenuation, such as at 12a-12g, the computer system will not recognize a fault condition.

Thus, every attenuation detected by the computer system will not indicate a fault and may simply indicate a pre-existing bend attenuation. Further, some signal attenuations will be slight, indicating a slight movement of the cable that does not indicate a fault. The Signal deviations that most concern a user of this system will be those that show a significant fault. The location of the attenuation on the signal will correspond to a location on the fiber optic cable where a fault may have occurred.

Figure 7:
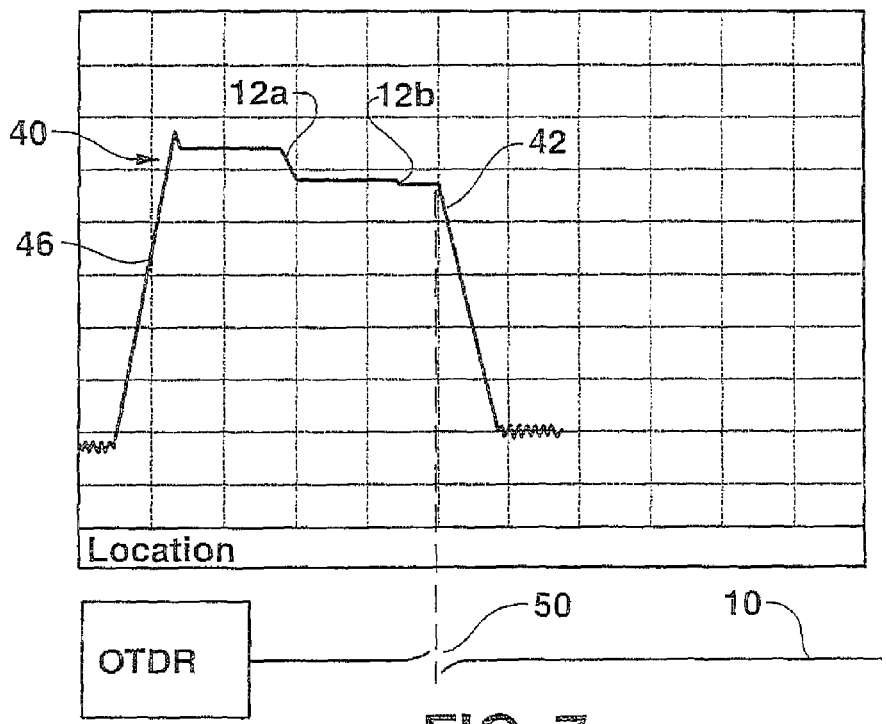
FIG. 7 is a graphic display of the OTDR signal when a fault condition has occurred in the barricade component of the security system, and a characteristic fault signal is produced.

As can best be seen in FIG. 7, in the event that a fault condition 50 is created in gate 10, fault signal 42 occurs in scan signal 40. Computer analysis involving a comparison of baseline signal D and fault signal 42 indicates an abrupt deviation in attenuation sufficient to create a fault signal. Computer 26 generates a fault signal which is delivered to display 32 in the form of a map or other information indicating the location of the fault condition which may be looked up in a computerized table. For example, an attenuation of −62D8 may represent a complete break in the optical fiber sensor line 12 and hence the barrier gate or grate. This information may be stored, as predetermined or signature fault signals, in a table format allowing for quick retrieval by computer readable instructions. A fault condition distance of 2,100 meters may be the location of an entrance gate to the secured area according to the location lookup table. A computer generated map may be quickly displayed at 32. Various ways of responding to the fault condition may be had at that time. For example, law enforcement personnel may be dispatched immediately to the location, various alarms may be activated, and other means of communicating the fault condition in a manner dictated by the security application being made.

Computer program 28 includes instructions for communicating with OTDR 18 and receiving repetitive scan signals, and analyses instructions for comparing the scan signals to the baseline signal which has been established. The instructions include lookup instructions for looking up the location of a fault signal in the event the analysis instructions determine a deviation from the baseline signal representing a signature fault condition. The lookup instructions look to see if the deviation matches the level of deviation required to indicate a complete break of the sensor line, material damage to the line, and/or other indicate conditions in the line which amount to a fault condition. The computer program may also include a map of the secured area and instructions to look up the location of the fault condition in response to the distance measured by the OTDR. Display instructions may include instructions for displaying the map and the location on display 32. Alarm instructions can be used to alert the attendant to the map display and the fault signal generally.

Figure 8:
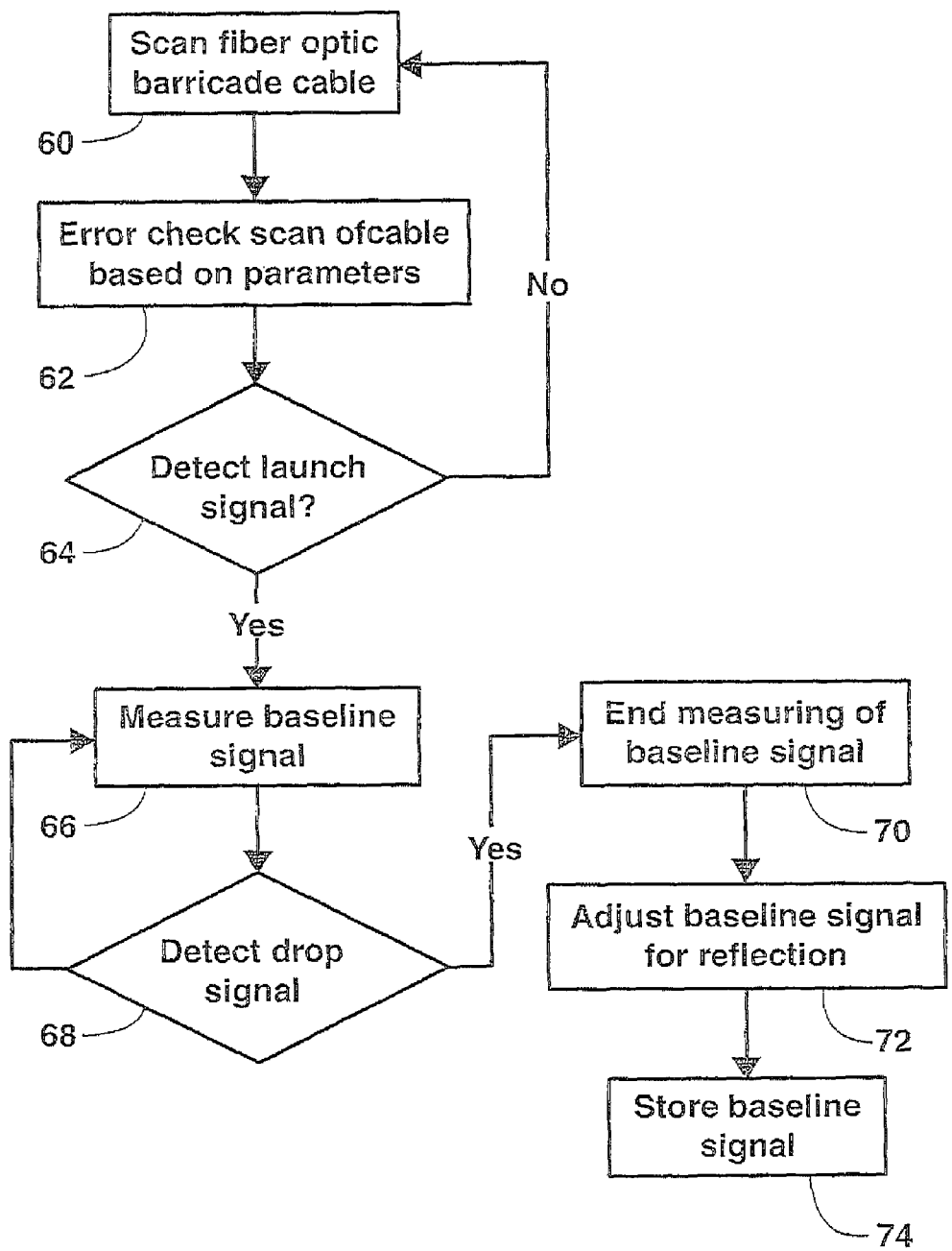
FIGS. 8-9 are flow charts for a security interface system for detecting a fault in the barricade security component and producing a characteristic signal indicating the location of the fault.
Figure 9:
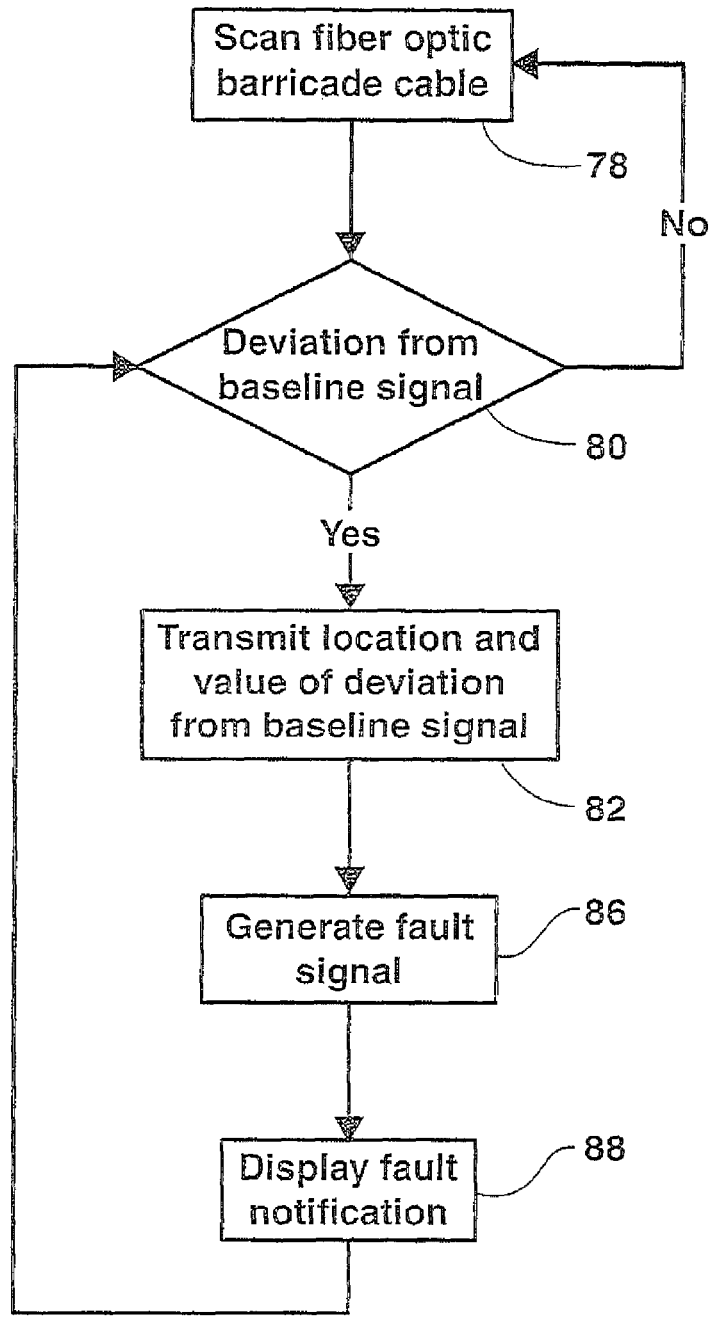

Referring now to FIGS. 8 and 9, flowcharts detailing the computerized operation of the security system are shown. FIG. 8 shows the initialization process of determining baseline D from scan signal 40 associated with barricade cable 10 in the security system. At step 60, the system initially scans fiber optic sensor line 12, extending through barricade cable 10. At step 62, the system error checks the information coming from the fiber optic line or cable. For example, a user may input parameters indicating the length of the cable to be scanned. If the length scanned by the system is greater or less than this parameter length, then the system will return an error and rescan the line from the start to ensure a proper base line is detected. Other parameters such as attenuations that should be found in the line may also be entered to assist in error checking. If a launch signal 46 is detected at step 64, the system will begin acquiring and storing baseline signal D in computer memory 30 at step 46. If the attenuation is not considered a launch signal, the system will continue to scan fiber optic line 12 until it detects a launch attenuation. The launch signal occurs when a significant rise from the noise floor occurs in the reading of the signal from the OTDR. Any insignificant attenuations simply indicate noise 44 and do not show the beginning or the end of the baseline signal.

Once the system has acquired a launch and begun measuring the baseline at step 66, it will continue to do until it detects a drop signal 50 at step 68. The drop signal is the inverse of the launch signal indicating the end of the baseline signal. The drop signal returns the scan signal of the fiber optic line to noise 44. At this point, the system will end acquiring the baseline at step 70. At step 72 the computer analysis adjusts the baseline signal for reflection. There is a distance immediately following the launch and immediately preceding the drop that is not a measurement of the baseline but rather a reflection signal at 52a and 52b occurring at the beginning and end of the line. This reflection is not considered an element of baseline signal 0, therefore, it is removed from the baseline signal at step 72. At step 74, the actual baseline is stored by the system in computer memory for comparison to future scan signals. The baseline is necessary in order to make all comparisons to future scans to determine a fault condition is occurring in the braided security cable of the barricade component.

FIG. 9 shows an overview of the normal operation of the security system while scanning the sensor line. After establishing the baseline signal, the scanning of the line will take place at step 78. The system will determine if any reflections, spikes or attenuation deviation from the baseline is detected at step 80 while scanning the sensor line. If no deviation from the baseline has taken place, the system will return to step 78 and continue to scan the line for a reflection deviations. Attenuation deviations do not necessarily have to indicate a fault. Sometimes attenuations will indicate the crimping or some other bend in the sensor cable. If these existed at the time of the determination of the baseline, then no action is taken if the attenuation found matches this baseline attenuation. If the attenuation does not match the attenuations in the baseline signal, the system will look up the deviation level from a data set stored in computer readable code, and determine if a fault signal condition exists. If so, the computer will generate a fault signal at 86. The fault signal can comprise multiple indicators. For example, an audible indication may be given to the user of the system indicating a fault. In a further embodiment, a visual indication may be given to the user indicating the location of the fault. In a further embodiment, the visual display may comprise a map with an indication at the point on the map where the fault has taken place.

Figure 10:
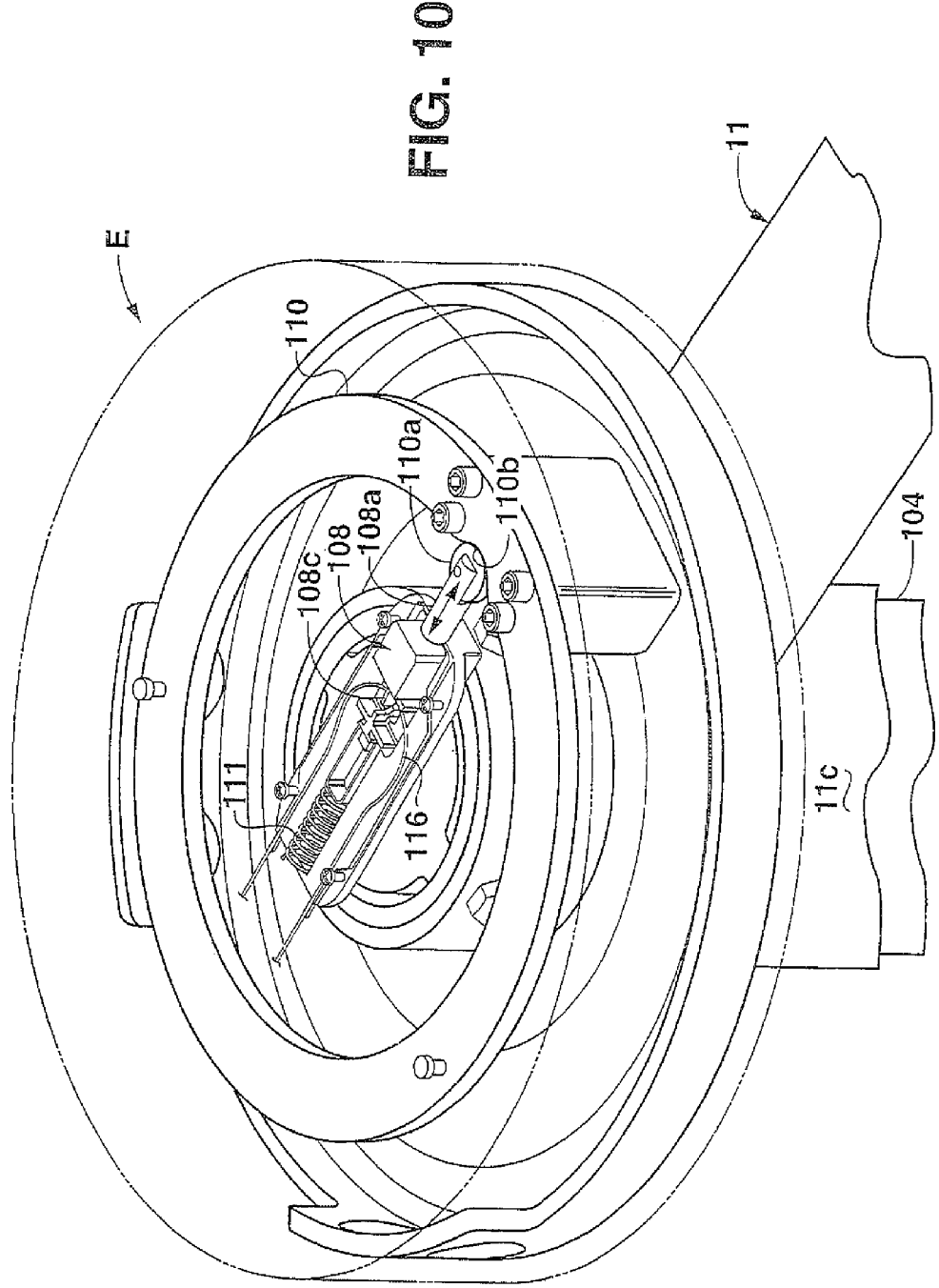
FIGS. 10 and 11 are perspective views of a barrier opening sensor constructed according to the present invention.
Figure 11:
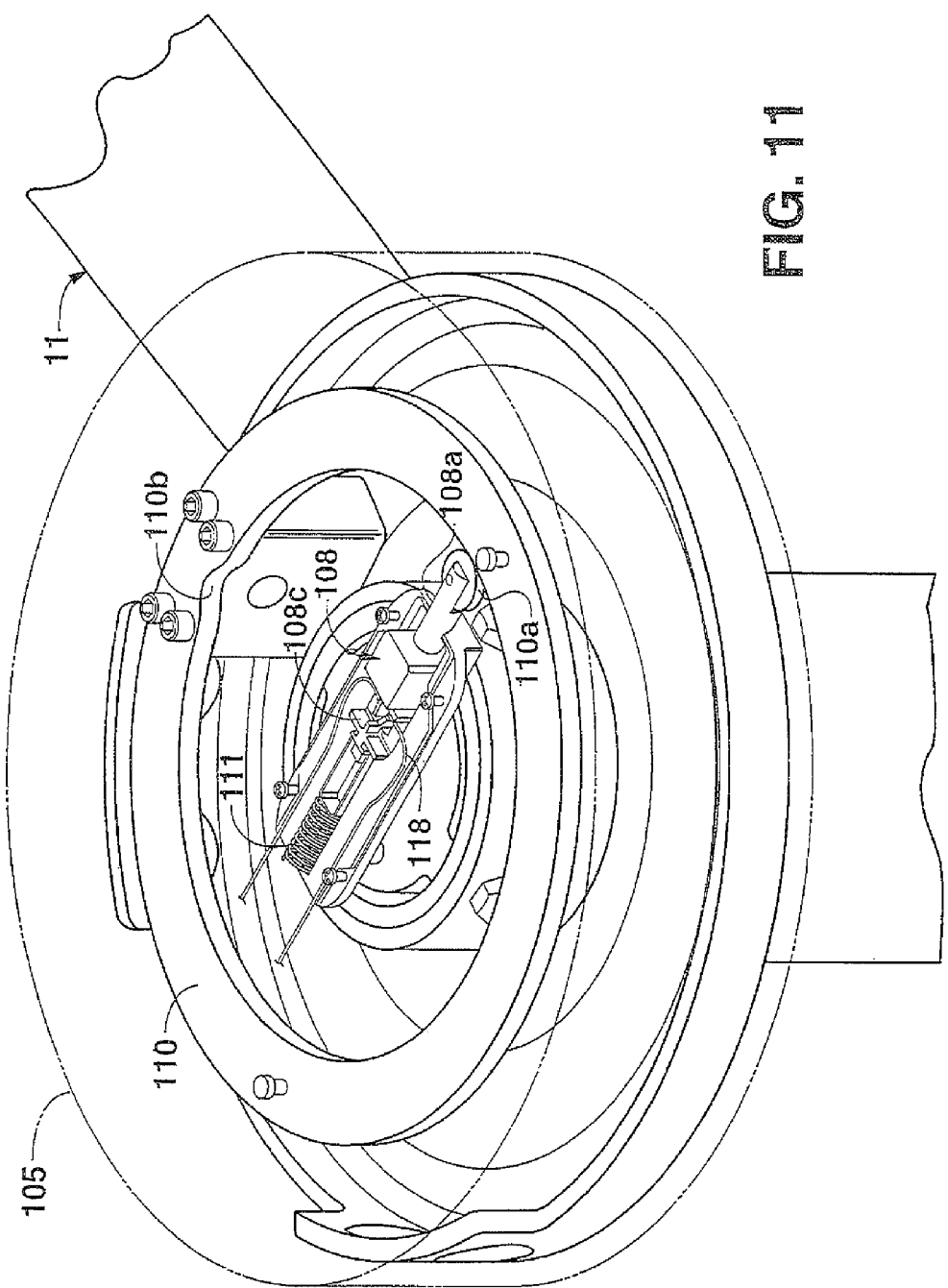
Figure 12:
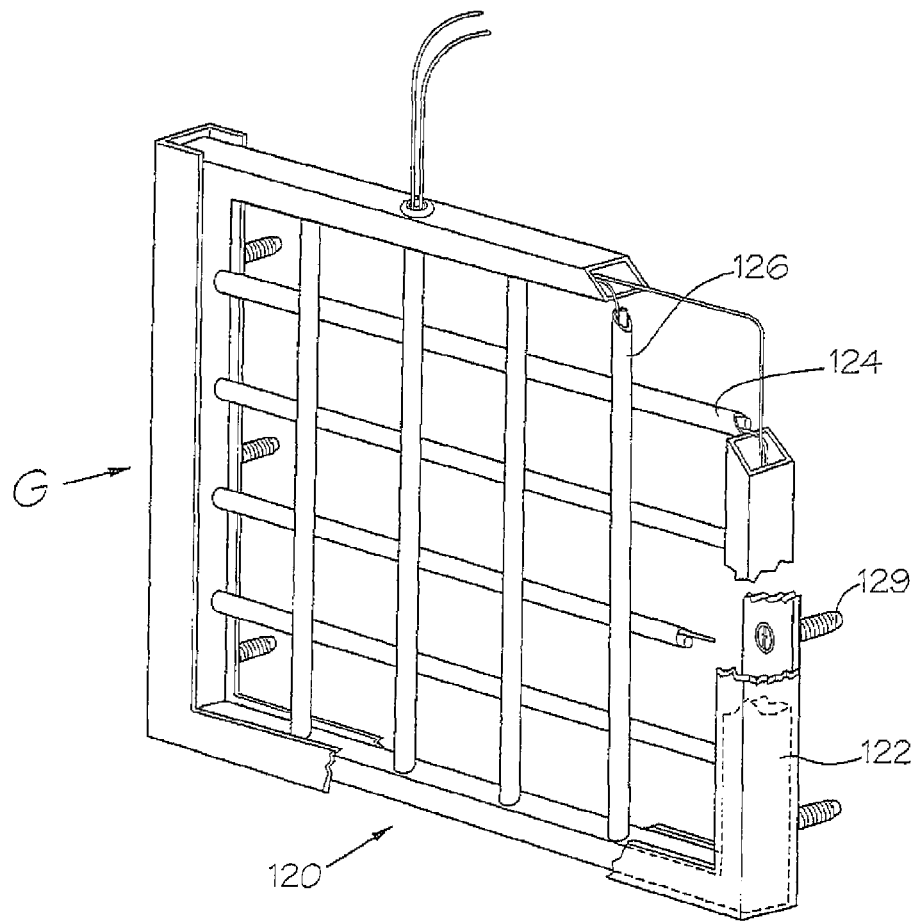
FIG. 12 is a perspective view illustrating a grate barrier and mounting frame constructed according to the present invention.
Figure 13A:
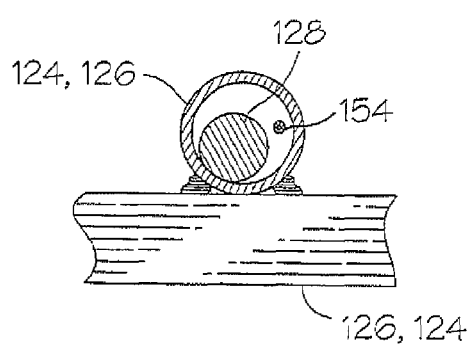
FIG. 13A is a sectional view illustrating a reinforced longitudinal tubular element enclosing a reinforcing member and an optical fiber sensor line according to the present invention.
Figure 13B:
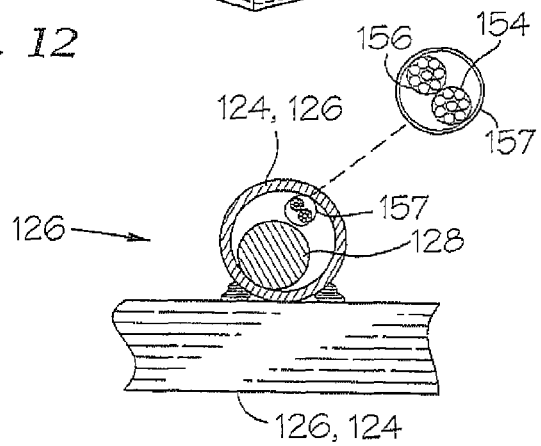
FIG. 13B is a sectional view illustrating a reinforced tubular element encasing a longitudinal reinforcing member and cable wrap enclosing two sensor lines for a double-end monitoring system according to the invention.

Referring to FIGS. 10-11, an embodiment of a barrier gate opening sensor in the form of a sensor unit E will now be described in more detail. The invention provides monitoring of vehicle or pedestrian gates on entrances in perimeter fencing or walls, barriers and gates on other entrances leading to a secured area, and between areas of varying security within a facility. There are two principle methods to breach an entrance barrier or gate; (1) opening the gate with a key, or by cutting the chain or locking device, or (2) cutting through one or more structural elements forming an element of the gate between the ends of the gate assembly, as described above. The invention provides a capability to detect either of these methods to breach a gate. When coupled with the software, both the nature of the breach and the exact gate involved can be ascertained from a remote monitoring location.

The opening and closing of gate 10 of gate assembly B is monitored by means of sensor unit E mounted on pivot post 104 supporting the gate components. This arrangement is illustrated in FIGS. 10 and 11. Sensor unit E includes a protective housing 105 mounted atop the pivot post of the gate assembly. Inside the housing is fiber optic cable sensor switch 108 having a reciprocating switch actuator 108*a*, and a cam in the form of a cam plate 110. As the gate opens or closes, the cam plate is turned. The sensor is 'tripped' when the cam plate is rotated from a closed position (FIG. 10) to an open position (FIG. 11).

As can best be seen in FIG. 10, cam plate 110 and sensor switch 108 are shown in the 'gate closed' position. The cam plate is attached to structural element 11 *c* which serves to rotate on pivot post 104 of the gate assembly and rotates with element 11 *c* as the gate is moved. A cam follower 110*a* is mounted to sensor actuator 108 which presses against optical sensor fiber line 16 when the cam rotates. When the gate is closed, the fiber sensor line rests in a normal loop 116 within the sensor.

In the illustrated embodiment, switch actuator 108*a* is slidably received in a housing block 108*b*. Sensor line 16 received in a cradle 108*c* having opposed contact surfaces between which the sensor like is received. In the closed position, the cam follower is urged into cam plate detent 110*b* by a spring 111.

As illustrated in FIG. 11, gate 100 has been opened. Now, cam plate 110 has rotated 90 degrees from the 'gate closed' position. Cam follower 110*a* moves inwardly causing switch actuator 108*a* to move so that a characteristic bend 118 is formed in the fiber. The computer processor detects this bend and recognizes it as a gate opening. The software 28 recognizes the specific entrance where the unlawful activity is occurring. Once gate 10 is opened and the fiber bent, opening the gate further will not change the signal produced by the fiber because the constant surface provided by the cam maintains a constant pressure by cam follower 110*a* on the fiber 16. When the gate is returned to its closed position, the sensor switch is returned to the gate closed position (FIG. 10). When the cam follower 110*a* returns to detent 110*b* in cam plate 110, pressure is no longer exerted on the optical fiber.

Referring to FIGS. 12 through 21, alternate embodiments of a grate barrier for different applications are illustrated. As can best be seen in FIGS. 12 through 15A, a grate barrier, designated generally as G, is illustrated having the particular advantages of detecting an attempted removal or cut through of the barrier, but delaying the completion of a severance a sufficient period of time to allow guard personnel to reach the culvert first. The assembly includes a grate barrier 120 and a mounting frame 122. The barrier is constructed as a grid of tubular steel structural elements 124 and 126 spaced on 6" centers and laced with single mode optical fiber 154, 156. While a single optical fiber can be used in certain applications and monitoring systems, in the preferred embodiment, two fibers 154, 156 are used in a "double end" monitoring system. Preferably, the fibers are wrapped in a cable wrap 157 it being understood, of course, that cable 157 can denote one or two optical fibers.

The horizontal tubular elements 124 and the vertical tubular elements 126 lie in two different planes, and are affixed in a barrier frame 128. In one example, the inside diameter of the tubular elements is 0.75 inches and the wall thickness is 0.062. The grate barrier is mounted in a mounting frame 122. The size and wall thickness of the frame are typically 1 inch by 2 inches and 0.084 inches respectively. This provides a robust grate assembly that is immune to false alarms due to wildlife, environmental forces, and causal human activity in the area. No electrical power is required at the grate barrier. The grate barrier may be located up to 25 km from the monitoring station.

As an important security measure, a plurality of longitudinal structural reinforcing members 128 are enclosed in the tubular elements 124 and 126. These reinforcing members delay barrier breakthrough after the sensor line is severed to allow sufficient time for guard personnel to arrive at the scene. Preferably, the reinforcing members are stainless steel rods encased in each vertical and horizontal tubular element having a diameter of 0.50 inches. The stainless steel rods provide additional delay even if the intruder is using a torch. Most of the delay will be after the fiber is broken by the cutting action. This gives responders extra time between the alarm and the intruder penetrating the secured area. The horizontal and vertical tubular elements are welded together at each crossover point, and lie in different planes. This reduces the number of right angle turns the fiber makes and decreases the probability of a false alarm, and also allows for encasement of continuous reinforcing members in both directions.

The grate barrier is installed using mounting frame 122 affixed to the culvert using tamperproof bolts 129. Preferably, the frame includes a "C" shaped channel 130 frame having three sides 130a-130c. The frame is installed, for example, on headwall 32 of a culvert 34 to form a frame into which the barrier is lowered. The barrier is contained on the sides and bottom much as a picture is slid into a three-sided frame. Tamper-proof bolts 129 have two heads. A traditional hex head is used to tighten the bolt during installation. Once the break-away torque is reached, this head will break free leaving only the featureless flat head to secure the installation. Preferably, Torque-LOC bolts available from Woven Electronics of Simpsonville, S.C., are used. Testing of these bolts has shown a delay time of 2 hours per bolt when perfect access is available. The bolts are located behind the barrier, as it sits in the "C" channel, making it impossible to get a tool on the bolts once the barrier is installed.

A service box 136 is installed on a side of the grate barrier to house fiber optic splices and provide an important security feature. A service loop 138 of optical fiber for the grate barrier is enclosed in the box. The service loop allows the grate barrier to be removed for required maintenance inside the culvert. To access the culvert, the service box is opened, and the service loop is extended to provide sufficient slack in the optical fiber to allow the removal of the barrier. The box also includes a splice board 140 for splicing the incoming sensor line(s) with the outgoing sensor line(s). Preferably the service box is alarmed with a tamper detecting, optical intrusion sensor 142 such as a Tamper-Guard optical sensor available from Woven Electronics of Simpsonville, S.C. The small, simple sensor Is mounted inside, adjacent to a door 136a of the service box in such a manner that any attempt to open the box will trip the sensor and the monitoring system, as will be more fully described at a later point.

Figure 15:
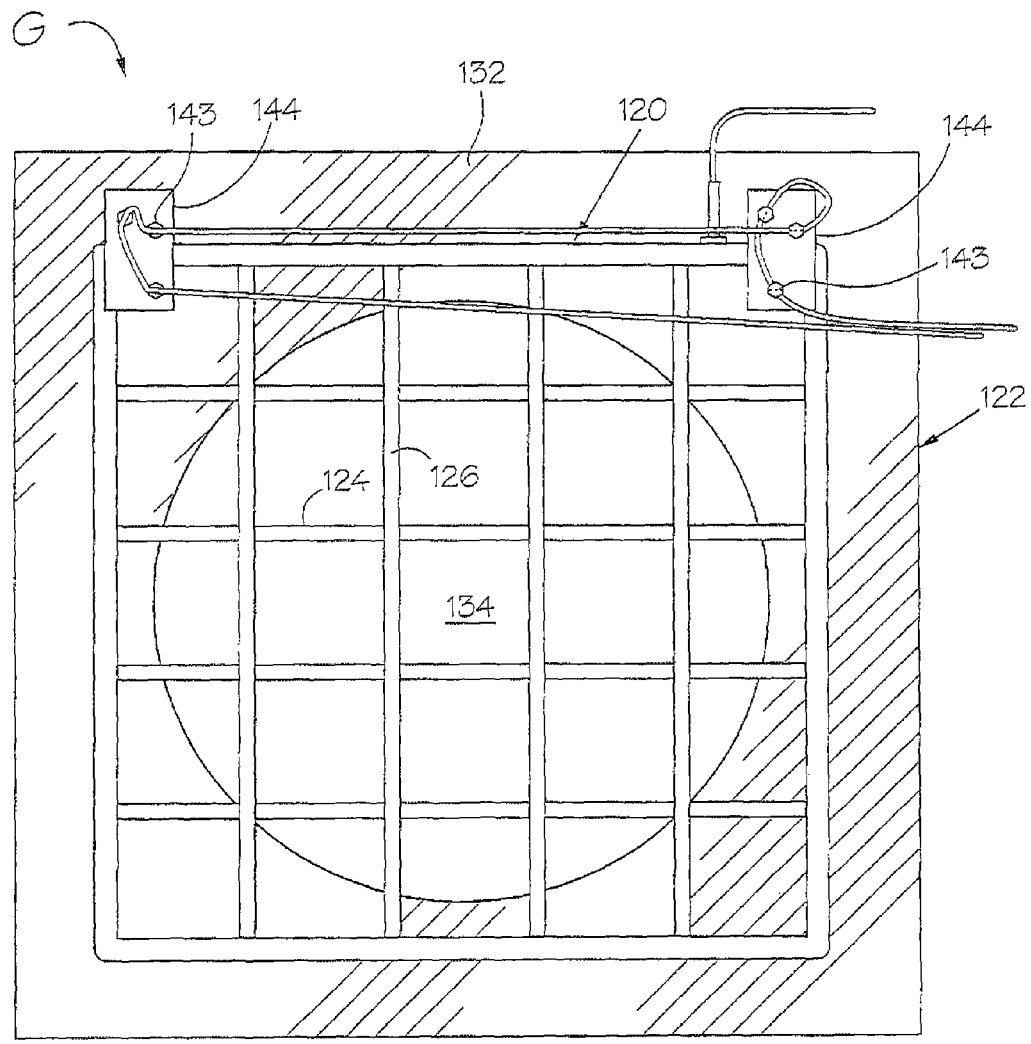
FIG. 15 is an alternate embodiment of a barrier grate assembly covering the entrance of a culvert and mounted thereto by bolts laced with an optical fiber sensor line.

FIG. 15 illustrates an alternate arrangement for securing barrier grate 120 over the culvert opening of culvert 134. In this embodiment, mounting plates 144 are attached over the open end of the three-sided C channel frame 122 and are attached to the hex head bolts 143 secured into the concrete headwall 136 of the culvert. Sensor line 157 is routed through openings in the hex heads of the bolts 143, as well as grate barrier 120. In this manner, the sensor line must be severed in order to remove the bolt. In addition, it is highly likely that the sensor line will be significantly bent in trying to remove the bolts so that a fault signal will be produced by the computer interface system either way.

An alternate embodiment of a grate barrier assembly, designated generally as H, is illustrated in FIGS. 16-17 which is used where there is no headwall to mount the barrier, and a potential for tunneling down through the sidewall of the pipe exists. In this case grate barrier assembly H may be provided with both "end" and "side" detection capability. As can best be seen in FIGS. 16A, 168, a circular grate barrier 146 is Illustrated having a grid of tubular elements 124, 126 framed by a circular tubular frame 147 attached at the entrance end of the culvert.

Figure 17A:
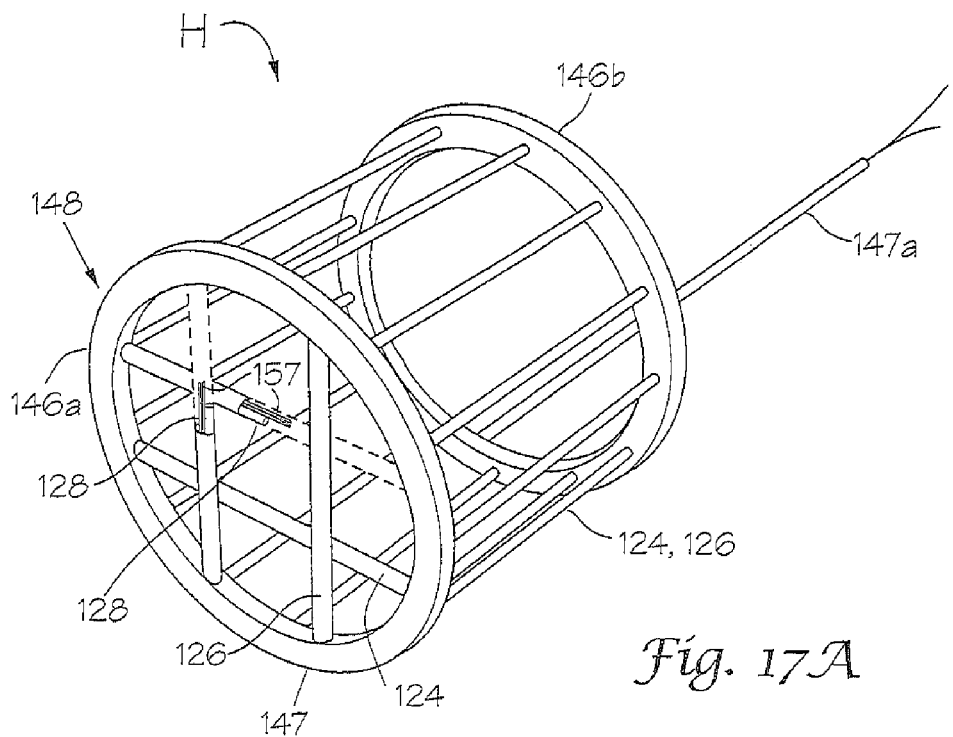
FIG. 17A is a perspective view of an alternate embodiment of a cage barrier which may be inserted at a point inside the culvert which is susceptible to dig-ins from the side of the culvert wherein the cage grate is laced with fiber sensor line and reinforced with solid bars.
Figure 17B:
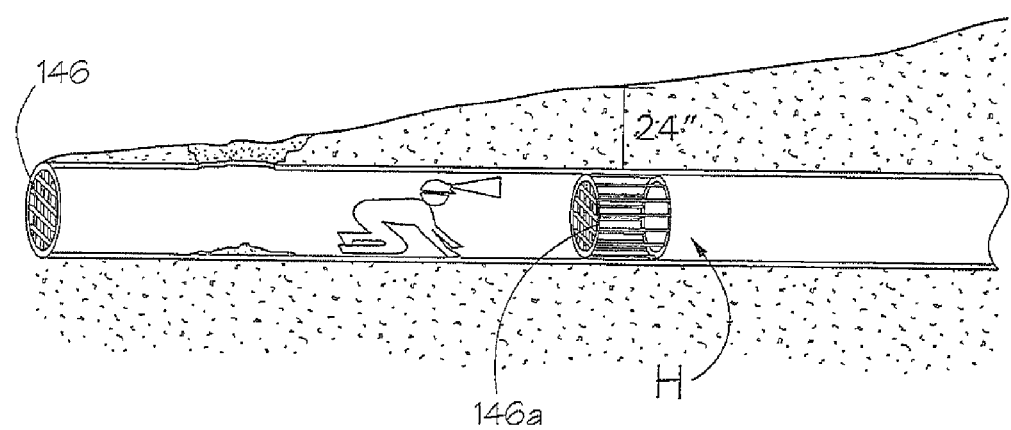
FIG. 17B is a schematic view of a side dig-in with the intruder confronting a cage barrier according to the invention.

FIGS. 17A, 17B illustrate a cage barrier 148 installed inside a culvert 147. The barrier is pushed up the pipe to a point where a "dig in from the side" risk is mitigated. The barrier also includes tubular elements 124, 126 around the perimeter of the barrier. The tubular elements are laced with fiber optic sensor lines to detect side dig-in intrusion attempts. It has been found that placing the cage barrier in the culvert at a point about 24 inches below the ground surface is effective for preventing dig-in intrusions. In the case of the entrance barrier or the cage barrier, the barrier is secured inside the pipe with tamper-proof bolts 129 to prevent removal. The bolts may be secured using any suitable concrete fasteners 129a drilled into the concrete for receiving the bolts. Removal from the pipe is also prevented by controlling the slack in the optical fiber. The slack is secured on the protected side of the barrier via a service box 136 as with a flat barrier. Any attempt to pull the barrier out of the pipe will put a strain in the fiber and will be detected. Grate barriers 146, 148 may be used alone or in combination.

Thus, it can be seen that robust grate barriers are provided at each location manufactured of steel tubing, reinforced with steel rods, and laced with optical fiber to detect tampering. Either control of the service loop with a tamper sensor 42 protecting the service loop, or security bolts laced with sensor lines prevents removal of the barrier.

Referring now to FIGS. 18-21, a preferred and alternate monitor for monitoring the optical fiber sensor line and detecting a fault condition representing an unauthorized intrusion attempt will now be described.

Figure 18A:
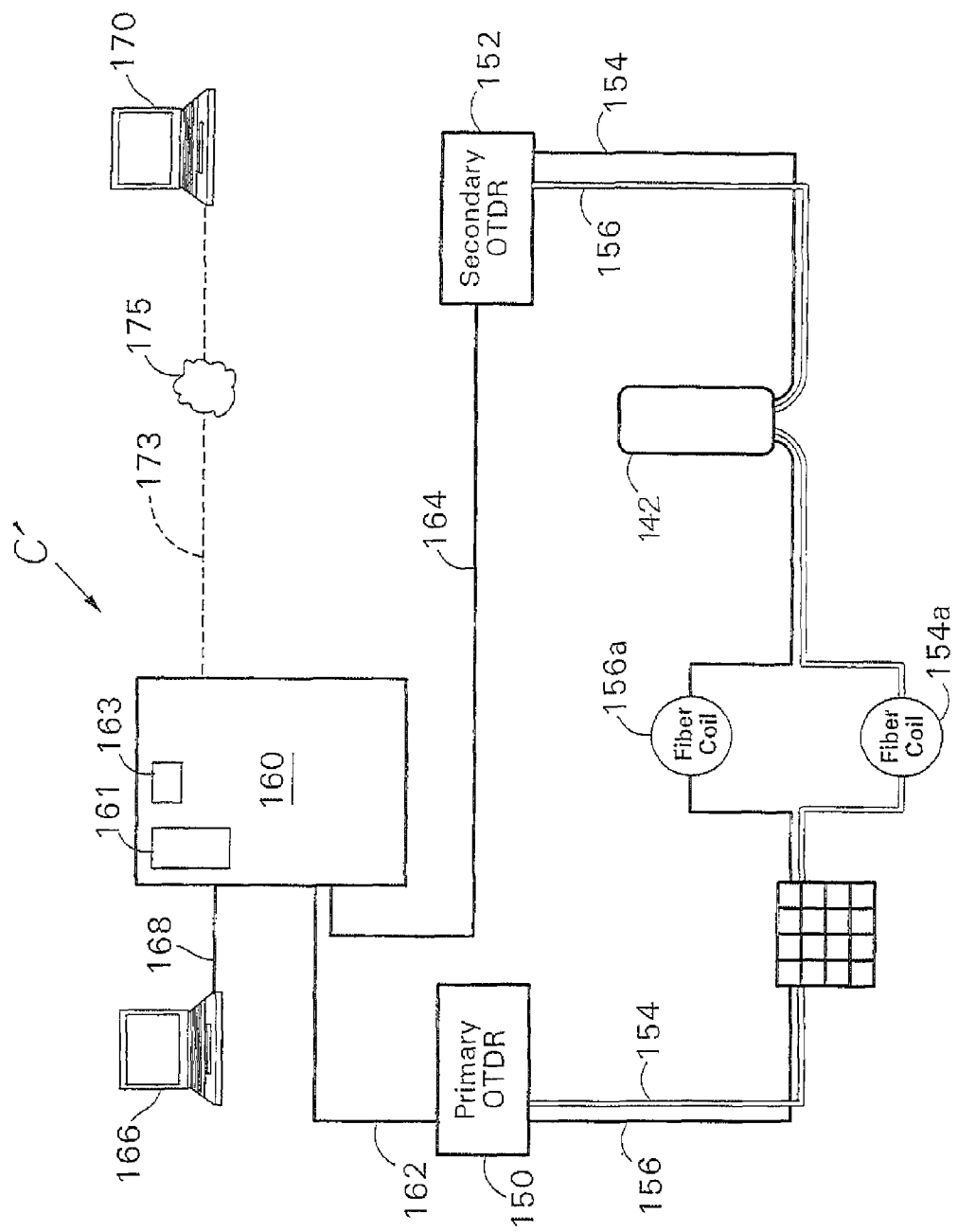
FIG. 18A illustrates a monitoring system utilizing two optical fiber sensor lines to provide a double end system that accounts for severance of the sensor lines resulting in both an upstream and downstream system.
Figure 18B:
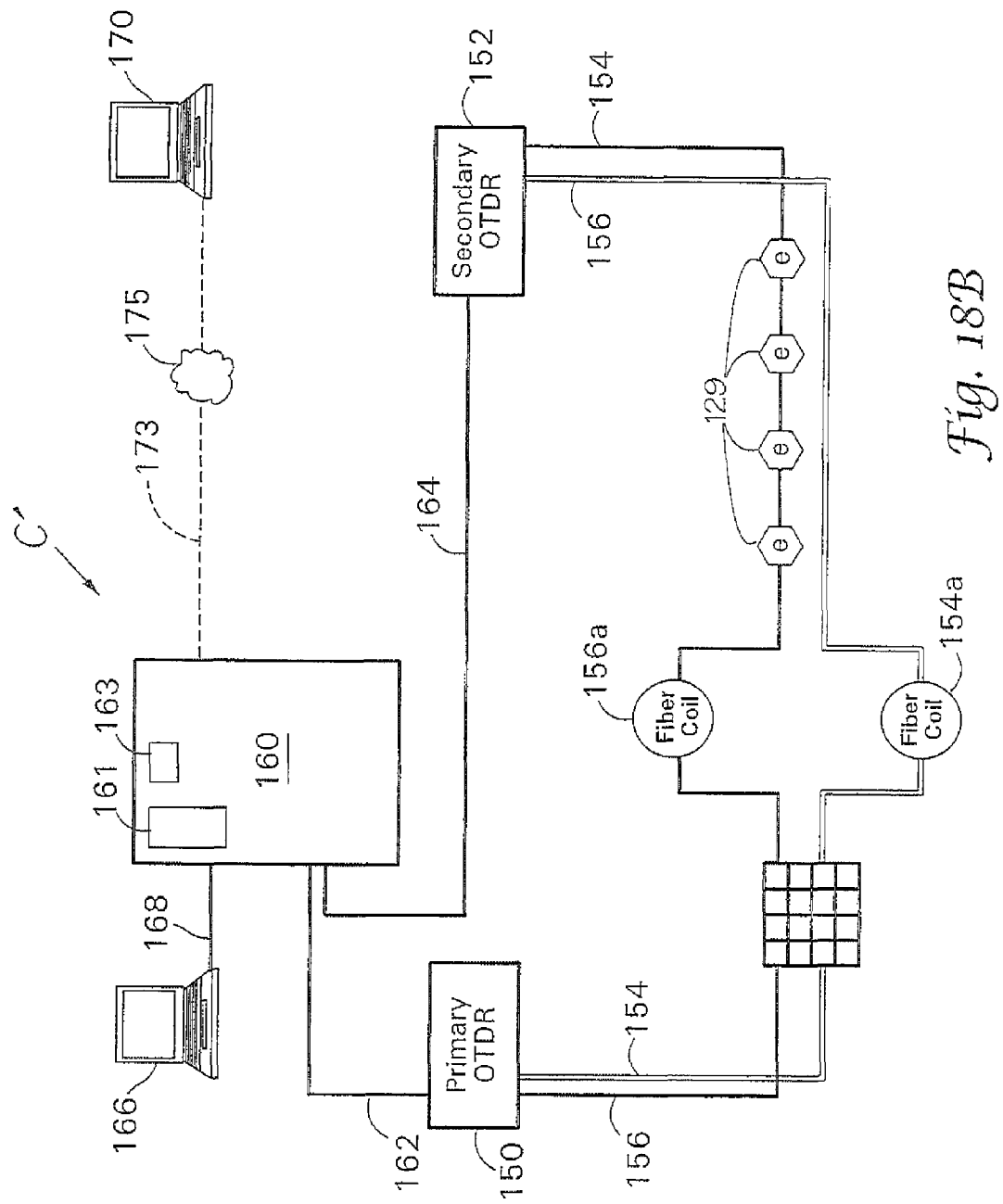
FIG. 18B is an alternate embodiment of a monitoring system having double-end capability utilizing security bolts rather than a door sensor to detect the opening of the grate.

As can best be seen in FIGS. 18A, 18B, a double-end optical fiber sensor line system monitor, designated generally as A', is illustrated for detecting intrusions and ensuring that a complete break in the fiber will not render the system inoperative. As illustrated, the system includes a pair of sensor line scanning units in the form of a primary OTDR 150 and a secondary OTDR 152 optically connected to first and second optical fiber sensor lines 154 and 156, respectively. Sensor line 154 Is operatively terminated at one end to the OTDR 150 and is connected in a non-terminated manner at OTDR 152. Likewise, sensor line 156 is operatively terminated at OTDR 152 and is connected in a non-terminated manner to OTDR 150. Other scanning arrangements and means may be provided such as a single unit combining the pulsing and scanning functions of two units, illustrated schematically in FIG. 20C. Both sensor lines are routed through either grate barrier 120, 146, 148, and sensor 142 or 143, and may be enclosed in cable wrap 157. However, as mentioned previously, the term sensor line may connote one or two optical sensing fibers, wrapped or unwrapped, unless specified differently, as herein. Primary OTDR 150 and sensor line 154 are connected to a system server/computer or processor 160 by means of a cable 162, and secondary OTDR 152 and sensor line 156 are connected to the computer by a cable 164. A computer monitor 166 is connected to the server by means of a cable 168. Optionally, a remote computer 170 may be connected to the server by means of the internet or other network. In the illustrated embodiments, door opening, intrusion sensor 142 (FIG. 18A) or a plurality of hex bolt intrusion sensors 143 laced with the sensor lines (FIG. 18B) are illustrated in series with a grate barrier 120, 146, or 148. In this case, a coil 154a of sensor fiber 154, and a coil 156a of sensor fiber 156 are provided between the barrier and sensor to provide optical separation. This optical separation allows the computer logic to differentiate between signals from the barrier and the sensors. The sensor lines may be routed through any number of barriers and intrusion sensors in a "daisy chain" arrangement as needed to secure a perimeter.

Primary sensor line 154 may be considered the primary line and normally senses an intrusion attempt by opening of service box door 136b and/or removal of a hex bolt 143. However, should the sensor line be cut and a complete break of the line occur, the sensor line 152 will continue to sense intrusions on a first, upstream side of the break, and sensor line 154 will continue to sense movement of covers on a second downstream side of the break.

Figure 19A:
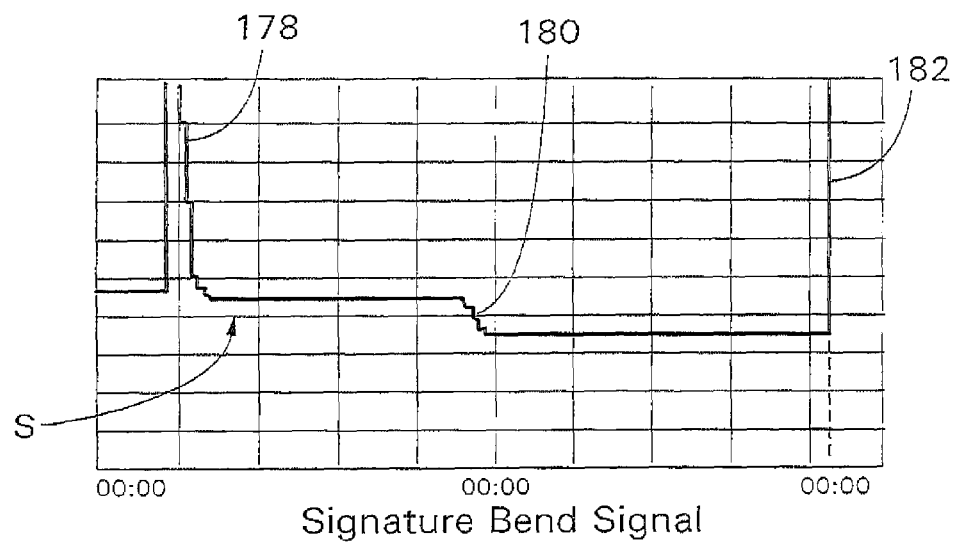
FIGS. 19A and 19B are schematic graph illustrations of signature signals that are preprogrammed in the system to be recognized as fault conditions according to the invention.
Figure 19B:
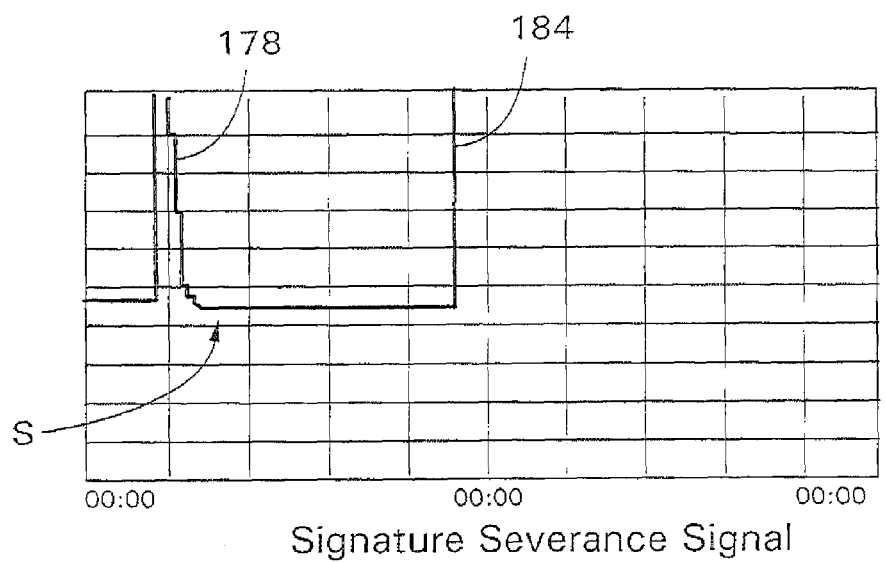

In operation, the primary OTDR emits a light pulse signal every 10 seconds, for example, and this pulse travels, down the optical fiber sensor line 154. The light travels to the end of sensor line 154 at the secondary OTDR and reflects back to the primary OTDR. As long as the reflections and attenuations match the reflection signal created when the system was installed, the OTDR waits till the appointed time and repeats the process. Should, the emitted light encounter an obstacle, a reflection is "bounced" back to the OTDR that does not match the reflection seen when the system was installed. Should light be lost (attenuated) from the fiber, this reflection occurs at a lower energy level, than was originally transmitted. This combination of reflections and attenuations defines a picture of the fiber sensor line, and this picture is called a signature. As long as the signature matches that of the original configuration of the system as established in the baseline signal, the software records the data and takes no action. The baseline signal is established as described in reference to computer interface system C. Illustrated in FIG. 19A is an OTDR trace showing attenuation in the light energy at a location that corresponds to the location of a service box 136 being monitored by the system. The door of the box has now been opened. We know that because the attenuation "dip" on the graph at 180 is the signature of an open door, or signature bend caused elsewhere in the systems. The system computer logic can differentiate these bends. A vertical spike in the graph at 182 is a reflection that indicates the end of the fiber. All light is reflected from the cleaved face of the fiber, thus the high reflective spike, indicating severance of the fiber.

The secondary OTDR fiber 154 is shown as black in the image to signify that the fiber is dark and not normally in use. Normally, secondary OTDR 152 and sensor line 156 are only used when there is a complete break in the sensor lines, as explained below. Preferably, the primary OTDR and the secondary OTDR are cycled by the processor every 24 hours so that the secondary OTDR and sensor line are dark for 24 hours and then the primary OTDR and sensor line are dark for 24 hours to ensure that both units remain in operational. Of course, while one unit is dark the other is operational with light pulse signals. While both units could be operated at the same time, it would serve no purpose.

Severance of the sensor line is known because spike 182 has "moved" on the graph from right to left at 184. When the software sees this signature of a break (a reflective spike) several things happen. Among these triggered events is the firing of the secondary OTDR 152 to pulse secondary sensor line 156. The secondary OTDR monitors secondary sensor line 156 housed in the same cable as primary sensor line 152 of the primary OTDR. The secondary OTDR can monitor the intrusion downstream from the break and the primary OTDR monitors those upstream from the break. This "double end" arrangement ensures that a break or severance in the fiber will not render the system inoperative. In similar fashion, the secondary OTDR will be fired if the primary OTDR fails and the system will remain operable. The signature intrusion signals are stored in computer readable code in the intrusion level data set for comparison to the periodic reflected pulse signals. The double-end system is described in more detail in U.S. non-provisional application Ser. No. 11/890,450, filed Aug. 6, 2007, entitled "Double-End Fiber Optic Security System For Sensing Intrusions, incorporated fully herein by reference.

The OTDR technology and software identifies every barrier and intrusion sensor, and its location, by its optical distance from the OTDR and monitor every meter of fiber anywhere in the system-fiber in the grate barriers, fiber in the tamper and intrusion sensors, fiber running out to the barriers, and fiber running between the barriers, and their locations. Damage anywhere in the system is detected and its location determined. In this system, multiple barriers and intrusion sensors can be "daisy chained" together on two pair of OTDRs. Two fibers would be laced through the barriers and sensors—one ODTR connected to each. This configuration provides complete redundancy to the system because no single point of failure exists. Additionally, the system provides map based graphic user interface and GPS location capabilities, fully adjustable breech and break alarms, email and pager alerts, remote PC visibility of the system's status, alerts, and complete event logging on the system.

A computer interface system C' for the double-end monitoring system includes a computer or processor 160, a resident computer program (software) 161 having features to process the detection and assessment of a pulse reflection and intrusion signal to determine the cause of the signal and select a response to the threat automatically. For example, in the case of the signature bend signal attenuation such as an open door shown in FIG. 19A the software can trigger a camera to see the specific reason that the manhole is being opened. This image will be captured and transmitted over the network to interested parties as a customer configured response to the assessment. In the second signature signal shown in FIG. 19B the cutting of an optical sensor line signifies a high priority threat at the location. In this case, the software may advise a response team of the status and location of the cut. This response can include initiating a "lock down" of all perimeter gates in response to the signature, and alerting off-site response teams as back-ups. Any number of sensors, signature signals, and responses may be programmed depending on the application being made. Assessment of the intrusion and initiating responses is a unique aspect of the present invention. The signature signals are stored in signature data set 163 in computer readable form and, for example, in a table look-up form. The data is stored in a computer memory accessible by the processor, and may also include response data used to signal a predetermined response to the proper personnel, a desired by the customer/user. The data is compiled by performing bending or damage to the fiber lines that would occur under prescribed intrusion attempts desired to be monitored and capturing the signature of the reflected pulse signal. The software tools match a reflected pulse signal deviation with one of the signature intrusion levels signals in the data set, a proper response to a change in a sensor line signal can be delivered. A suitable computerized system and program is disclosed in U.S. non-provisional application Ser. No. 11/083,038, filed Mar. 17, 2005, entitled "Apparatus And Method For A Computerized Fiber Optic Security System," now published as International Publication Number WO 2006/05277 A2, on May 18, 2006, commonly owned and incorporated by reference into this application. The system recognizes the different signature signals received from the OTDR on the basis of predetermined rules, and interprets the real event that caused the signal. The system also allows the use of multiple sensors to be recognized simultaneously by the system and unique baselines to be identified by sensor type, location, etc. The system can discern the difference between authorized and unauthorized activity. The programmed processor has the ability to catalog predetermined events on the basis of the reflected signals and recognize them as either authorized or not authorized when (and where) they occur.

Referring now to FIGS. 20A through 20D, alternate embodiments of system monitors are illustrated and will now be described.

Figure 20A:
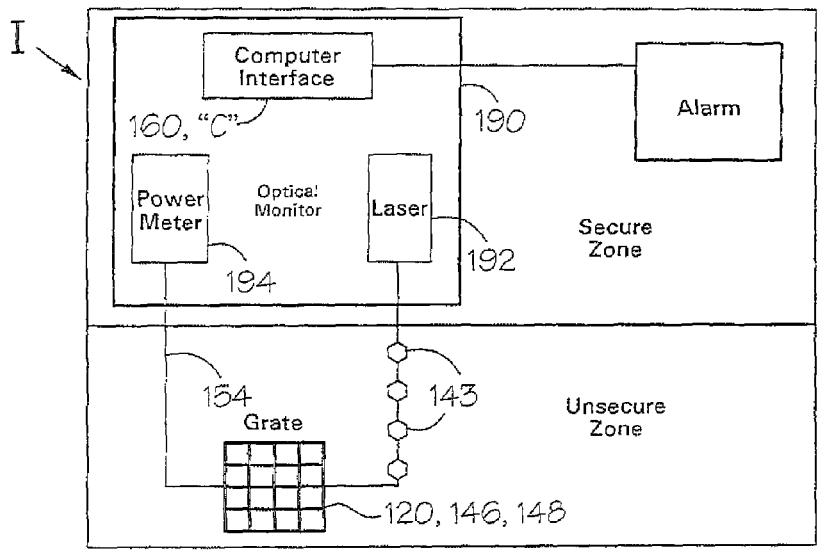
FIG. 20A is an alternate embodiment of the monitoring system according to the invention.

As can best be seen in FIG. 20A, a system, designated generally as I, is illustrated having a monitoring unit 190 connected to a grate barrier 120, 146, or 148. This is a simplified system, monitoring only a barrier and/or other sensor. Monitoring unit 190 is provided for monitoring the fiber or sensors while detecting events above a preset threshold from the baseline within a second. The monitor unit can differentiate between a triggered sensor event and a fiber break event, or fault condition. The monitor evaluates a monitored signal relative to its particular secure state. This secure state, called a baseline, may be easily taken and saved by the user. For this purpose, the monitoring unit includes a laser 192 that transmits a line along an optical fiber sensor line 154 which is received by a power meter 194 that senses the light received after passing through the lacings of the grate barrier and barrier removal sensors 143 (or 142). Upon the occurrence of any predetermined deviation or severance of any of the tubular elements and sensor line the fault condition is analyzed and a visual or audible notification is produced for warning.

Figure 20B:
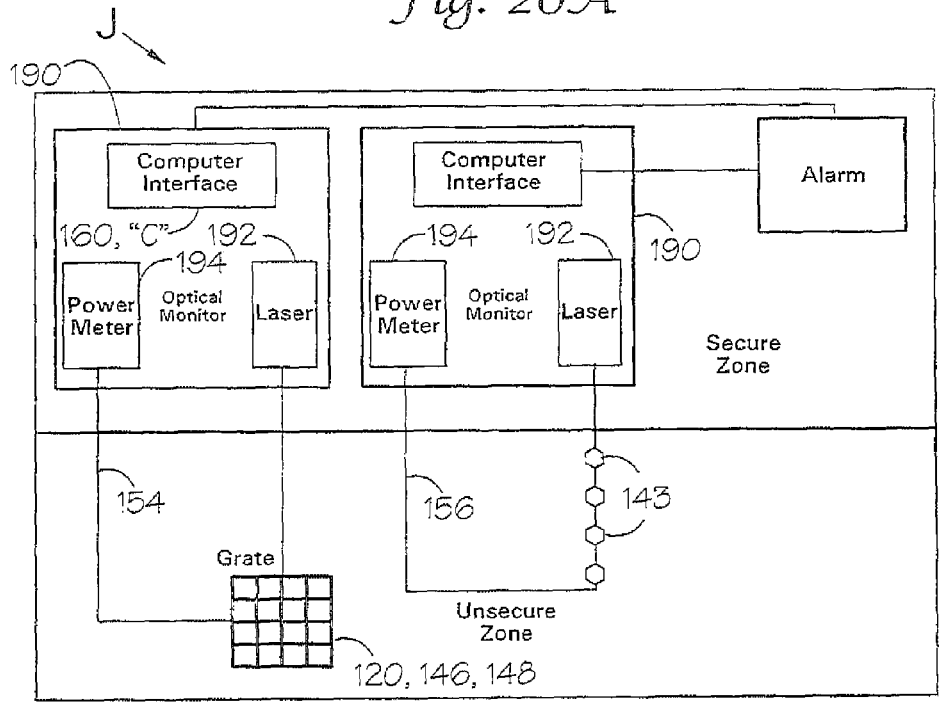
FIG. 20B is an alternate embodiment of a monitoring system employing two separate monitor units according to the invention.

FIG. 20B illustrates a system monitored, designated generally as J, which includes a separate optical monitoring units 190. The first unit 190 is connected to the grate barrier, and the second unit 190 is connected to the sensor line running through the intrusion sensor bolts 143 (or sensor 142). This provides two separate systems for monitoring the barrier cut through and removal. This embodiment may be advantageous in certain applications where it is desired to have separate system monitors.

Figure 20C:
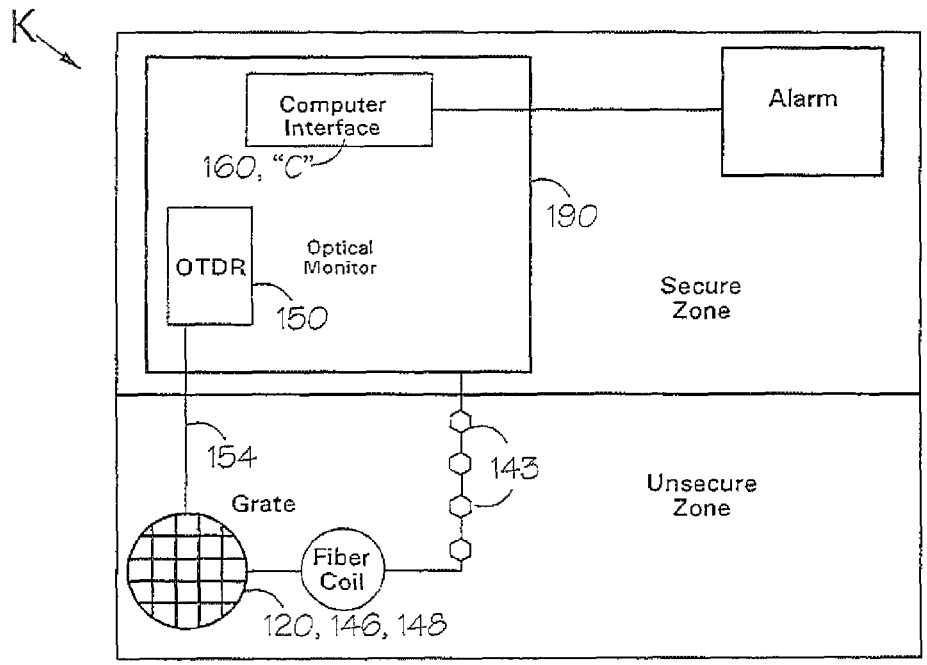
FIG. 20C is an alternate embodiment of a monitoring system according to the invention employing only a single sensor line and OTDR monitor.

Referring to FIG. 20C, a system monitor, designated generally as K, is illustrated which utilizes a single OTDR 150 to monitor a grate barrier and intrusion sensor bolts 143 (or sensor 142). This single end system is desirable in some applications as opposed to the double-end system described previously.

Figure 20D:
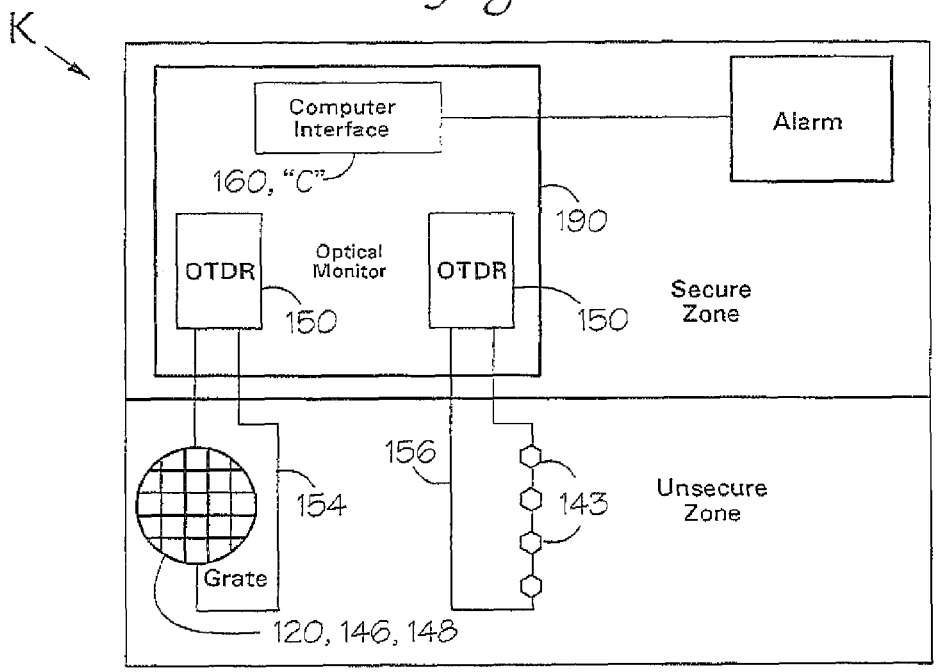
FIG. 20D is an alternate embodiment of a monitoring system according to the invention employing two sensor lines and OTDR monitor.

FIG. 20D illustrates yet another alternate embodiment of a system monitor, designated generally as L, where two separate OTOR systems are utilized to monitor first the barrier grate cut through, and secondly an attempted removal of the barrier either by intrusion sensor bolt removal or opening of the service box (sensor 142).

Any suitable monitoring unit 190 may be utilized in the above monitoring system such as a Light-LOC Express module unit available from Woven Electronics of Simpsonville, S.C., which may be referred to for more detail. The Express Monitor includes relay switches embodied as a processor connected to indicator lights indicating a breach and/or a break of the sensor line and grate. If the signal deviates from a first threshold corresponding to a breach, the signal is sent to the breach relay which switches the breach indicator light on and activates an audible or visual alarm. If the signal deviates from a second threshold corresponding to a break, the break light is turned on. Thus, the breach and break lights may be on. Thus, the current sensor signal (voltage) is compared to the baseline in the processor. The baseline is set by reading the receiver when the system is in a secured state, and stored as a voltage. When the current sensor reaches a threshold value (fault level) the appropriate relay is switched. The signal and threshold value by be above or below the baseline. When the monitor is cutoff and later back on, the baseline is reset. Relays may also include one for a momentary breach alarm and momentary break alarm. When the module is powered up, the baseline is reset to monitor the configured system. This is performed by simply switching it on and then turning it back to its original position.

Figures 21A, 21B:
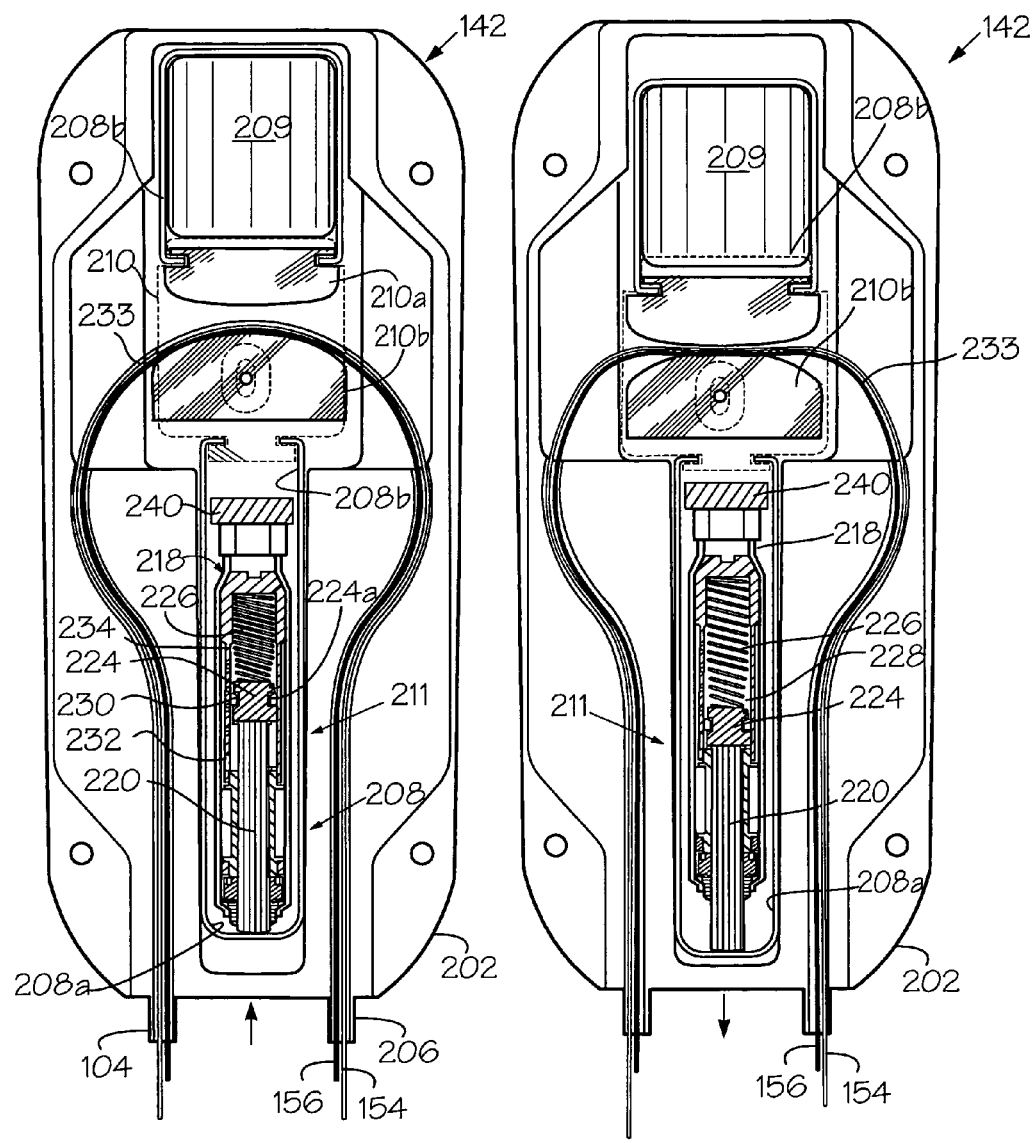
FIG. 21A is a front elevation of a film optic intrusion sensor with the front cover removed showing the sensor in a non-activated condition.
FIG. 21B is a front elevation of a film optic intrusion sensor with the front cover removed showing the sensor in an activated condition.

Referring now to FIGS. 21A, 21B, an embodiment of a fiber optic intrusion sensor 142 is illustrated which includes a housing 202 having a fiber entrance 204 and a fiber exit 206. A moveable carrier, designated generally as 208, is illustrated which includes a lower strap 208*a*, an upper strap 208*b*, secured together by means of a sensor block 210. Sensor block 210 includes a lower adjustable abutment 210*a* and upper abutment 210*b* which produce the natural and characteristic bends in the sensor fiber. The slid able carrier 208 moves between a normal deactivated position as shown in FIG. 21A in which the carrier is raised by magnetic attraction between magnet 209 and the removable member (box lid 136*a*) to its upper most position. In FIG. 21B, the carrier is shown in its downward activated position caused by interruption of the magnetic attraction between magnet 209 and the removable member.

In order that a quick opening and closing of the removable member results in a discernible signal that can be detected by the processor, e.g. OTDR 12, a signal control device is provided to shape the signal so that any signal generated by the sensor has a prescribed minimum pulse duration (width), regardless how quickly the manhole cover is removed and replaced. In the illustrated embodiment this is accomplished by a delay mechanism, designated generally as 211, in the form of a fluid cylinder 218 that delays the movement of carrier 108 to the deactivated (uppermost) position following movement to the activated (downward} position. Thus, the deflection of the fiber optic back to its natural state is delayed. In the illustrated embodiment, means for delaying return of the fiber optic to its natural shape so that a pulse width of sufficient duration for sampling is generated under the control or shaping provided by delay hydraulic cylinder 218. The signal control device produces a signal having a prescribed minimum pulse width that has been determined to be reliably recognizable by the processor. For example, a minimum pulse width of 15 seconds is necessary for recognition and sampling by a typical OTDR. To ensure reliable detection, the control device is preferably set to produce a minimum pulse duration of 45 seconds. Thus, even if the intruder drops the cover quickly, for example after seeing the sensor, a recognizable signal is transmitted to the processor.

Delay cylinder 218 includes a piston head 224 at the end of piston rod 220 having a check ring 224*a*. A compression spring 226 is carried between piston head 224 and an upper end of a fluid chamber 228 in which oil, or other hydraulic fluid or gas, is enclosed. Delay cylinder 218 is positioned between an abutment 240 affixed in housing 202 and bottom strap 208*a* to act as a shock absorber to delay the return of carrier 208 to its deactivated position. A suitable cylinder 218 is manufactured by Enidine Incorporated of Orchard Park, N.Y.

In operation, in the normal position of sensor 142, slidable carrier 28 is in its up position which urges piston 20 upwards into cylinder compressing spring 226. When the magnetic attraction is broken by sufficient movement of the manhole cover, piston head 24 quickly moves downward as the spring decompresses. In this situation, fluid either bypasses check ring 24*a*, or exits a major port 22 so that sensor fiber 14*a* is deflected quickly to form its characteristic bend 233 producing a signal. In order that the pulse width of the signal is sufficient to detect, even if the cover is placed back quickly, the ascent of the carrier is retarded. This is caused by the fact that in order to reach its normal shape in the normal position of magnet 209, fluid pressure must be overcome, as well as the compression of spring 226. Thus, as carrier 208 moves upward causing piston rod 220 to move upward, piston head 224 is caused to force fluid out through the restricted, minor orifices 230 into passage 234, as well as to compress spring 226. This delays the termination of the signal sufficiently so a pulse width is provided that can be detected by the OTDR. This is particularly advantageous if a large number of sensors are utilized along a fiber network having a long distance so that activation of a plurality of sensors can be detected generally concurrently even if the closure member is quickly replaced. Sensor 142, and system therefore, is described in more detail in U.S. non-provisional application Ser. No. 10/429,602, filed May 5, 2003, entitled "Fiber Optic Security System for Sensing Intrusion of Secured Locations;" and PCT application no. PCT/US2004/013494, filed May 3, 2004, entitled "Fiber Optic Security System For Sensing The Introduction Of Secured Locations;" incorporated fully into this application by reference.

As disclosed in FIG. 4 of the application, the grid of the grate may be composed of or tubular elements extending in one direction with the sensor line being woven through one, down the other, etc. FIG. 5 illustrates a grid of intersecting tubular members with the sensor line routed through the intersection of the tubular element where they cross one another. As can best be seen in FIGS. 22 through 24, an entrance barrier H having a grid 248 composed of a plurality of intersecting structural tubular elements 250 and 252 is illustrated wherein the tubular elements 250 intersect the elements 252 extending transverse to the tubular elements 250 in a common plane. At a cross-intersection 253, there is a through-hole at the opposing ends of tubular elements 252. The sensor line extends through the ends 252A and 252B and through the tubular members 252. Since the sensor line is routed through a tubular member 252 and then exits the tubular member and enters the entrance of the adjacent tubular member the runs of the sensor line in the direction of the first and second tubular member will cross each other at cross-intersection 253.

Entrance barrier H coextends with the entrance to prevent entry by an unauthorized intruder wherein the grid of first tubular elements 250 and second tubular elements 252 intersect one another in a common plane. The first tubular elements have through-hole openings 260 formed in aligned opposing sides of the tubular elements. The openings provide a means for a through-hole routings at cross-intersection 253. The ends 262 of the second tubular elements are affixed to the through-hole openings of adjacent first tubular elements 250. A first continuous routing channel 264 extends through the first tubular elements 250 and a second routing channel 266 extends through the second tubular elements 252 by means of the aligned through-hole openings 260.

Figure 22:
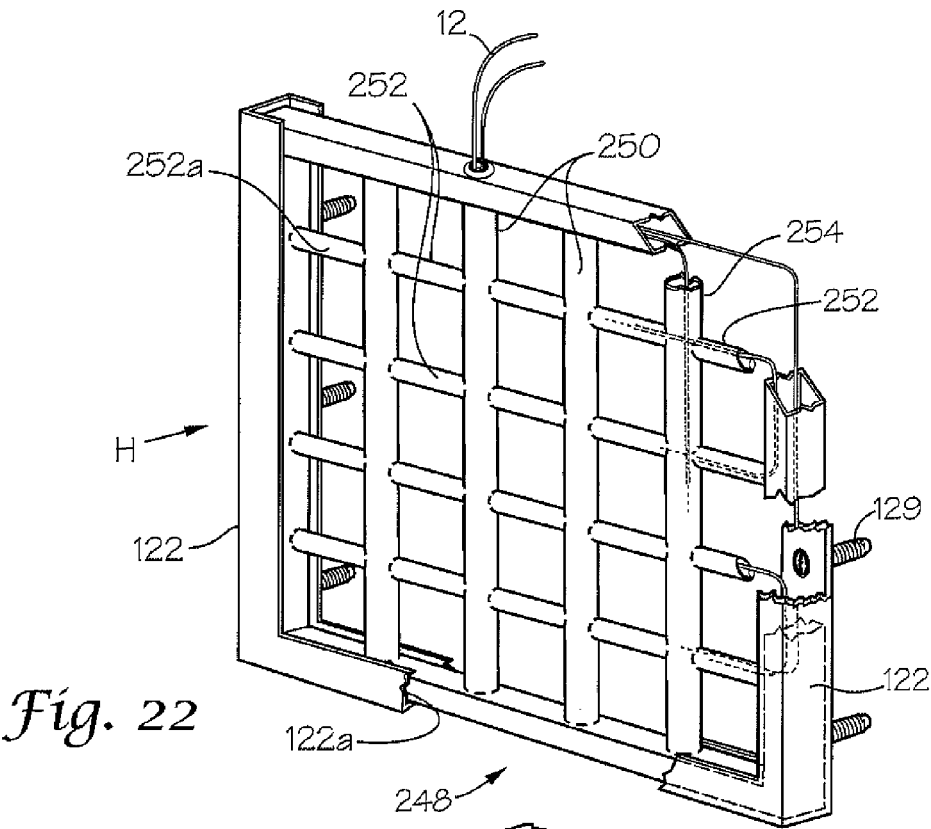
FIG. 22 is a perspective view with parts cut away showing the grate of FIG. 5 in more detail.
Figure 23:
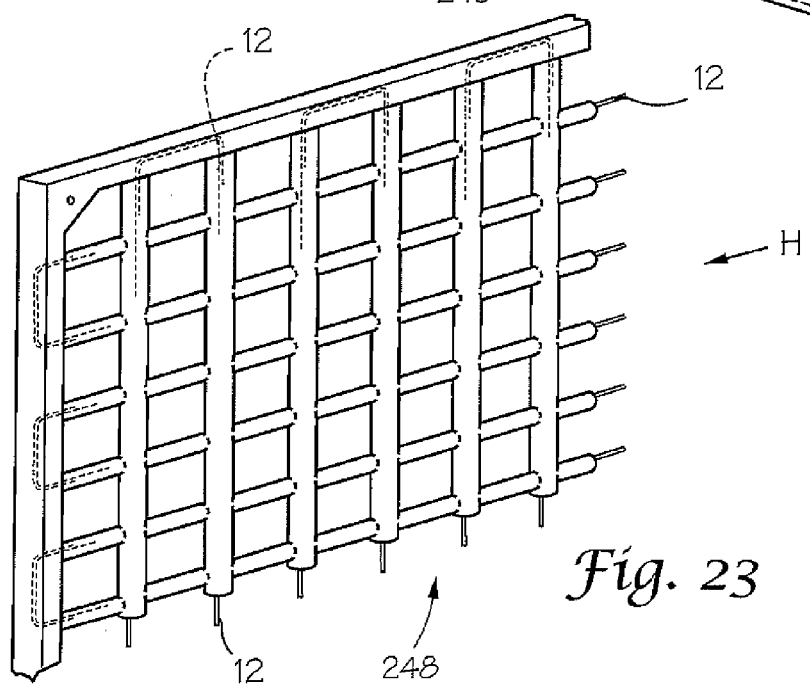
FIG. 23 is a partial view of the grate of FIG. 22 illustrating the cross tubular elements being smaller than the vertical tubular elements.
Figure 24:
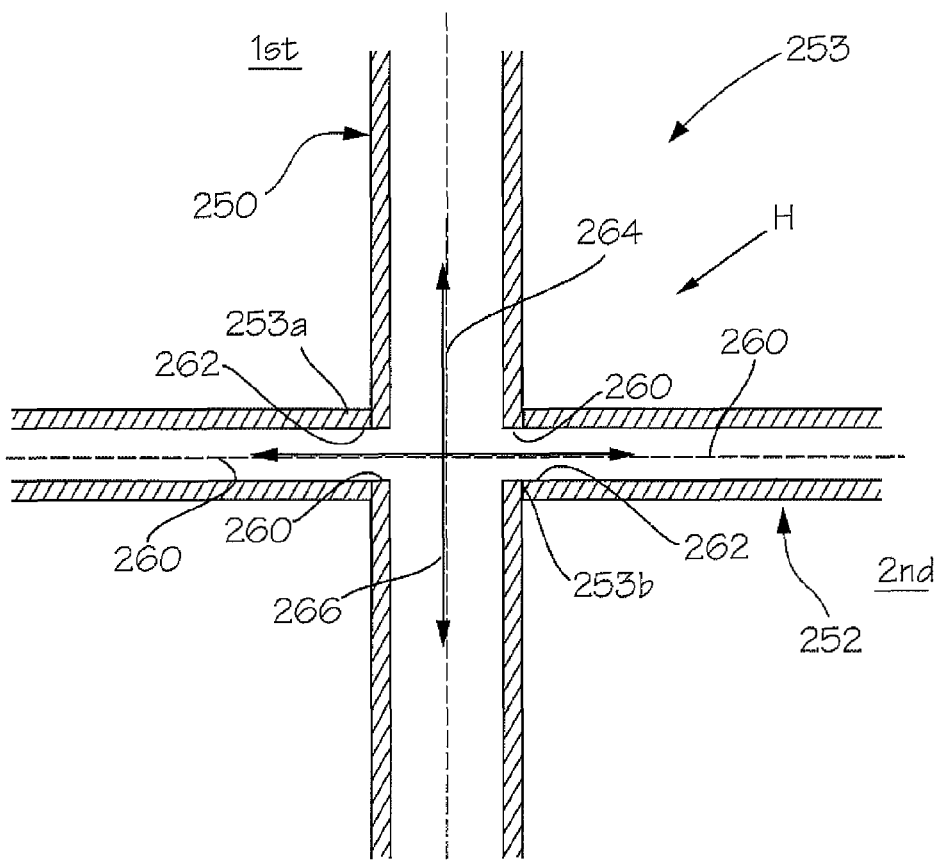
FIG. 24 is an enlarged sectional view cross tubular of the area shown in FIG. 5.
Figure 25:
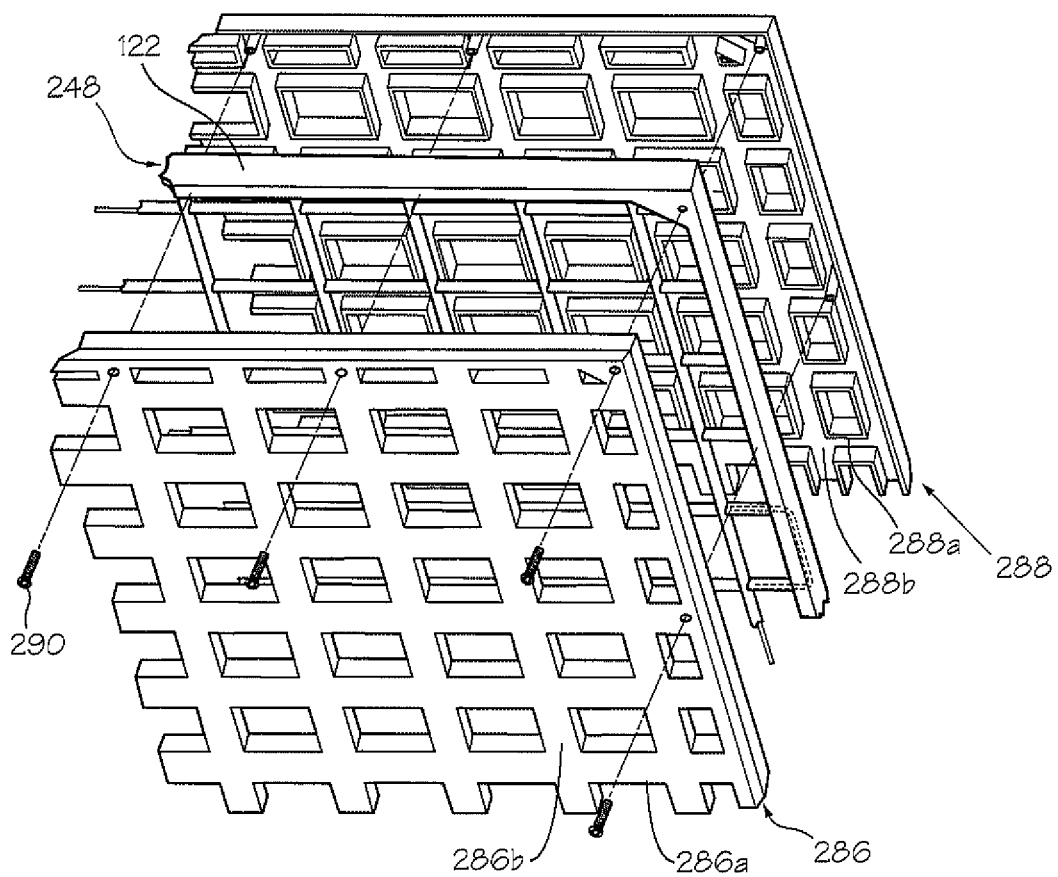
FIG. 25 is a front elevation of an encasement unit with the encasement section separated.

Referring to FIGS. 22 and 23, it can be seen that routing frames 122 are fixed around the perimeter of the grid. The routing frames have routing channels 122a communicating with the open ends of the first and second tubular elements. In this manner the sensor line 12 may be routed in and out of the routing openings of the tubular elements while protected by the routing frames. Optionally, the first and second tubular elements may also include a rigid reinforcing rod extending through the tubular elements which must be cut through in order to sever the sensor line and the tubular elements, as disclosed in FIGS. 13A and 13B above.

Preferably for an advantageous construction of the tubular elements which intersect in a common plane, the second set of tubular elements may have a smaller diameter than the first tubular elements so that they may be welded or joined together more easily.

Figure 26A:
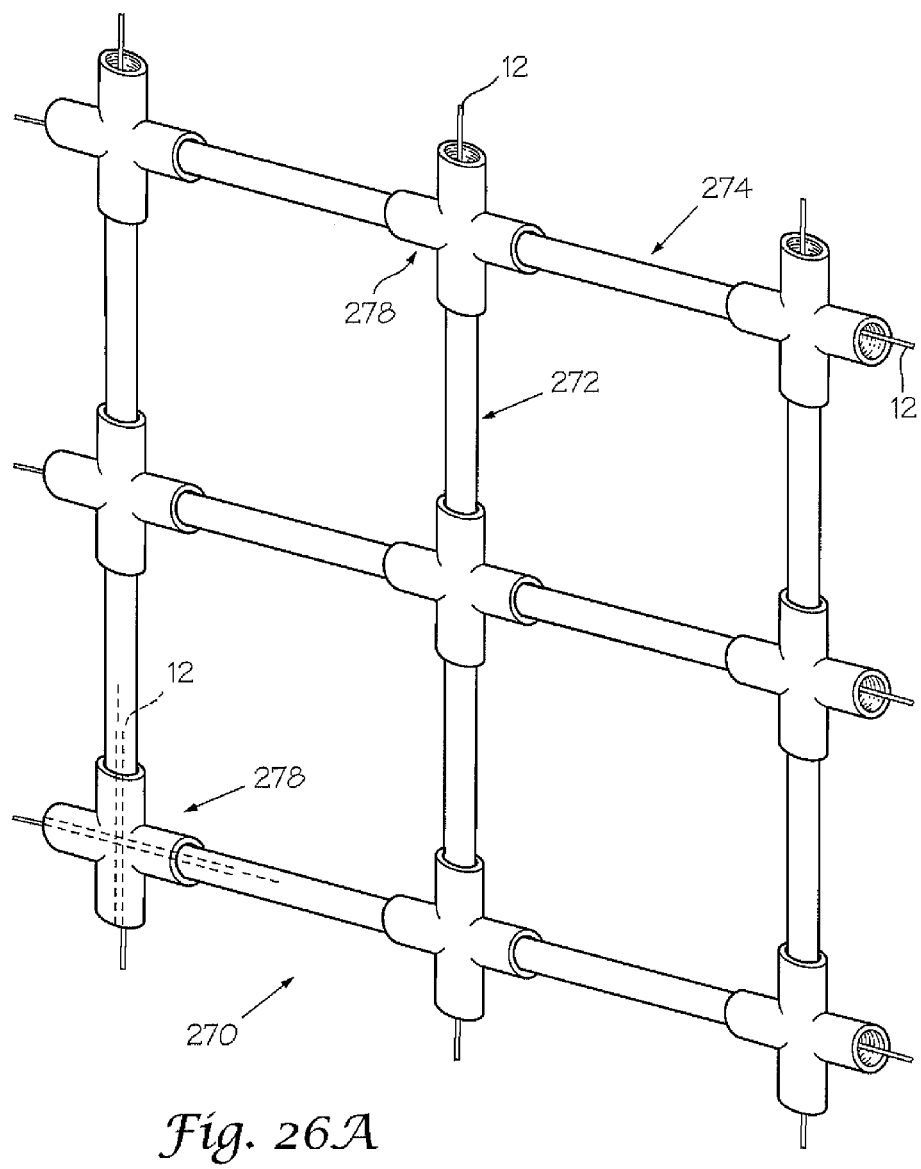
FIG. 26A is a front perspective view of a grate according to an invention wherein the tubular elements and cross-fittings are PVC pipe.
Figure 26B:
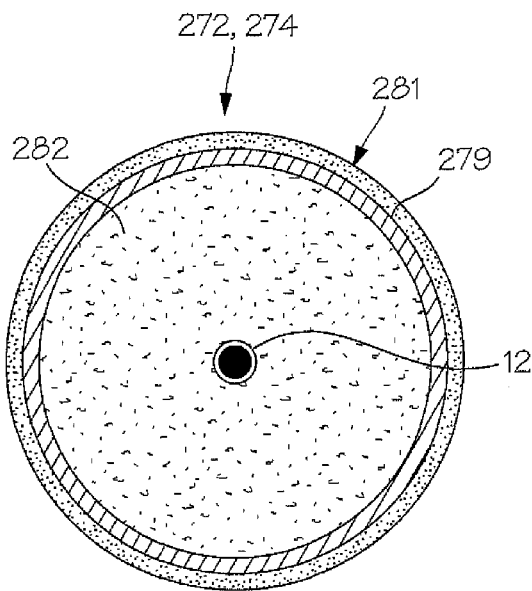
FIG. 26B is a cross sectional view of the PVC pipes of FIG. 26A.
Figure 26C:
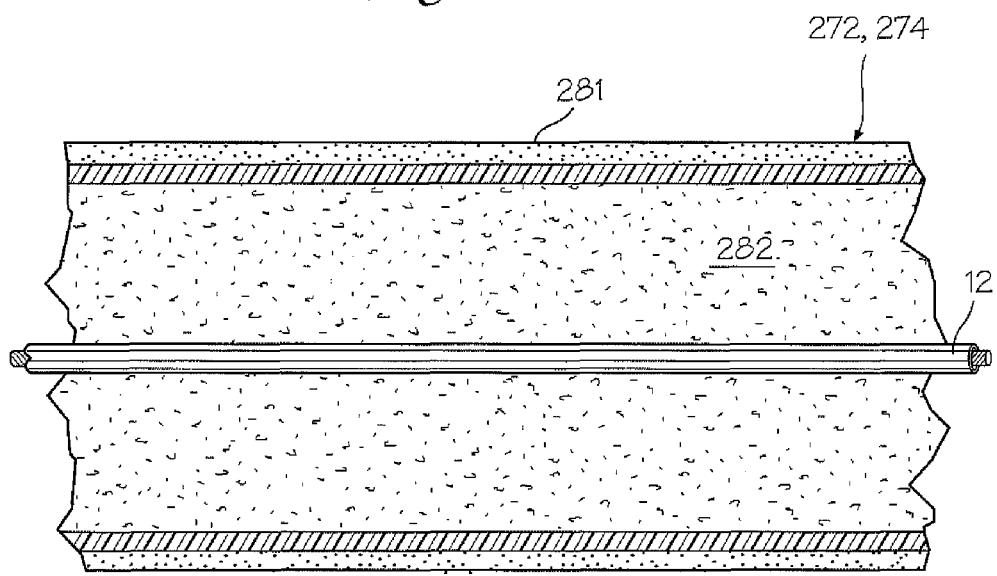
FIG. 26C is a longitudinal section of the PVC pipe showing the back filling in the pipe.

In another embodiment of the invention, as can best be seen in FIGS. 26A-26C, a grid 270 is made of PVC pipe wherein first tubular elements 272 comprise a length of PVC pipe, and second tubular elements 274 comprising PVC pipe. In this case, the cross-intersection where the sensor line crosses itself is provided by a cross fitting 278 for PVC pipe is provided at the intersections of the pipe and at the ends. Thus, the tubular elements are continuous across their length or width since the four legs of the cross fitting receive open ends of the tubular elements. The PVC tubular elements and cross-fittings/sections are assembled without glue to assure the fitting of a well aligned planar grate. The pipes and fitting would dry too quick and probably be misaligned out of plane if PVC glue was used during assembly. Therefore, after assembly, the PVC grate is sprayed with a solvent to fix the parts together at the joints between the pipe and legs of the cross-fitting. Any suitable solvent can be used, such as a polyacrylate. Preferably, the PVC grate includes a coating or layer 280 of a UV-resistant material after the solvent. Any suitable UV-resistant layer material 281 can be used such as a polyurea. As can best be seen in FIGS. 26B, 26C, the pipes can be back filled with a suitable material 282 for stiffening the structure and providing additional structural integrity. A suitable fill material is precision grout which flows easily into the gaps and cracks, and hardens so firm it can be machines.

In another aspect of the invention, in the underwater application of the barrier grid, an encasement unit 284 comprised of a suitable plastic or other material which resists barnacles and other underwater encrustments is made in first and second fitting sections 286 and 288. The sections encase the barrier grid and tubular elements thereof. The sections 286 and 288 include matching channels 286a, 288a and cross-channels 286b, 288b which have the same pattern as the intersection tubular members 250, 260 whereby the tubular elements are sandwiched between the two sections. The sections may be fastened by fastener 290 of any suitable type. When deployed under water, the encasement protects the tubular elements against accumulations of barnacles and encrustations and the like. When the encasement unit needs to be replaced, the barrier grid may be removed from the water and a new encasement placed on the grid.

Thus, it can be seen that a highly advantageous construction for a security system and intrusion sensors can be had according to the invention where fiber networks can be utilized to provide optical fiber sensor lines routed through barriers and/or sensors connected in series and terminated with an OTDR device or other monitor, to determine the occurrence and location of an intrusion anywhere along the fiber optic lines. In this manner, the entire network may be secured against terrorists or other acts of invasion, vandalism, etc. The fiber optic monitoring system maintains the ability to recognize specific signals on a common fiber(s) and segregate those that are authorized from the signals that denote unauthorized activity. Currently, the invention can recognize at least nine different signals on the fiber. These signals may occur on the same fiber, or separate fibers. As illustrated, the system may function with both contact and non-contact sensors. The software instructions can uniquely detect intrusion with both contact and non-contact sensors simultaneously. In either case, the intrusion detection is accomplished by interrogating the light reflected out of the fiber when a sensor is triggered. The system provides for multiple sensors to be "tripped" at the same time and the invention will track the status of each independently. In the standalone system where a single location is monitored, a monitoring unit having an established baseline and one or more thresholds corresponding to fault conditions may be used. Many advantageous forms of grate can be used with the detection system.

While a preferred embodiment of the invention has been described using specific terms, such description is for illustrative purposes only, and it is to be understood that changes and variations may be made without deelementing from the spirit or scope of the following claims.

What is claimed is:

1. A security system for detecting an unauthorized activity and attempt to enter through an entrance of a secured area comprising:

an entrance barrier for controlling entry through the entrance including a plurality of intersecting structural tubular elements;

at least a first intrusion sensor, including a sensor line, for sensing a first predetermined fault condition corresponding to an unauthorized attempt to move the barrier;

a second intrusion sensor, including a sensor line, for sensing a second predetermined fault condition corresponding to one of a bend or a severance of a tubular element;

at least one monitor unit for transmitting a sensor signal along the sensor line, and at least one receiver unit for receiving the sensor signal upon return;

a monitor processor for receiving said sensor signal from said receiver unit and initially establishing a baseline level corresponding to the state of the sensor line in a secure condition, detecting when said sensor signal reaches a threshold level above the baseline level, and generating a fault signal in response to reaching or exceeding the threshold level corresponding to one of a movement, a bend, or a break in the sensor line; and a notification device communicating notice of the fault signal to security personnel.

2. The system of claim 1 wherein said second intrusion sensor senses said sensor line being physically impacted by damage to said tubular elements causing the sensor signal to reach the threshold level signifying said first fault condition.

3. The system of claim 1 wherein said plurality of intersecting tubular elements includes first tubular elements intersecting with second tubular elements wherein said first and second tubular elements lie in different planes.

4. The system of claim 1 including a security mount for mounting said barrier in one of a position over an entrance to a culvert and within an interior of a culvert wherein said first intrusion sensor is associated with said security mount to sense a removal or attempted removal of said barrier.

5. The system of claim 4 including a service housing located adjacent said mounted barrier containing a service loop of the sensor line that must be extended to remove said barrier, said service loop being enclosed behind a door of said service housing, and said first intrusion sensor includes a door opening sensor disposed inside said service housing whereby one of opening said door and severing said sensor line between said barrier and service housing causes a fault signal to be detected and generated by said system computer.

6. The system of claim 1 wherein said barrier includes a cage barrier mounted within said interior of the culvert space longitudinally from an entrance, said cage barrier includes a face grate of said intersecting tubular elements laced with said sensor line transverse to said culvert interior, and a plurality of longitudinally-extending, laced perimeter tubular elements spaced around a perimeter of said cage grate so intrusion from a side dig-in into the culvert is prevented.

7. The system of claim 1 including a longitudinal reinforcing member encased within said tubular elements along with said sensor line, said fiber sensor line being laced through said tubular elements alongside said reinforcing members whereby a complete cutting of said reinforcing member delays complete severance of said tubular element required for entry after severance of the sensor line and generation of a fault signal whereby guard personnel is provided sufficient time to arrive at the scene before intrusion.

8. The system of claim 1 wherein said processor includes a plurality of predetermined fault levels corresponding to fault conditions including one of a break, bend, and movement of said tubular elements and/or said grate, said processor including an initial baseline level which corresponds to the state of the sensor line in an undisturbed secure state, a plurality of threshold levels above or below said baseline level which correspond to a fault level, wherein said processor detects a current sensor signal reaching or exceeding a threshold level, and wherein said processor determines said baseline level when the processor is turned on and is reset each time the processor turns off and on.

9. A security system for detecting an unauthorized activity and/or attempt to enter through an entrance of a secured area comprising:

a sensor line;

an entrance barrier including a grid of first tubular elements and second tubular elements intersecting one another having hollow interiors and lying in a common plane;

a plurality of cross-intersections formed by said first tubular elements and second tubular elements intersecting one another and forming a cross-through passage for crossing of said sensor line through said tubular elements;

said sensor line extending through said first tubular elements and crossing over the sensor line extending through said second tubular elements at each said cross-intersection; and a monitoring unit comprising a signal transmitter for transmitting a sensor signal along said sensor line, a signal receiver for receiving said sensor signal, and a processor for processing the current sensor signal to detect a deviation in said sensor signal representing a predetermined fault condition;

whereby any predetermined deviation or severance of any of the tubular elements and sensor line is detected and a visual and/or audible notification may be produced for warning.

10. The system of claim 9 wherein said entrance includes a barrier frame disposed along a portion of the periphery of said barrier, said frame having routing channels communicating with open ends of adjacent first and second tubular elements, and said sensor line passing through said routing channels to lace in and out of said tubular elements so that the sensor line extends through said first and second tubular elements.

11. The system of claim 9 wherein at least one of said first and second tubular elements include a rigid reinforcing member extending through the tubular elements which must be cut through in order to sever said sensor line and/or the tubular elements so that entry is delayed upon generation of a sensor signal representing a tampering with the tubular elements.

12. The system of claim 9 wherein said first tubular elements and said second tubular elements include intersecting plastic pipe; and said cross-passage includes a cross-section fitting receiving the ends of the first and second tubular elements at the intersection thereof.

13. The system of claim 12 wherein said plastic pipes include a filler material wherein said sensor line is embedded in said filler material.

14. The system of claim 13 wherein said plastic pipe is PVC pipe and said filler material includes precision grout.

15. The system of claim 9 including an encasement unit having first and second encasement sections being constructed and arranged to fit together and encase said grid of first and second tubular elements to resist and protect the grid against accumulations of encrustations, barnacles, and the like when deployed under water so that the encasement unit may be removed from the grid and replaced when needed while the grid remains protected.

16. The system of claim 9 wherein sensor line includes an optical sensor line, and Said processor receives and processes the sensor signals from said signal transmitter in real-time representing the state of the current sensor line, and generates a real-time fault signal in response to detecting one of a first and second predetermined fault conditions; and a notification device communicating notice of the fault signal to security personnel.

17. The system of claim 9 including a security mount for mounting said barrier over an entrance including an intrusion sensor associated with said security mount to detect movement of the barrier; said intrusion sensor being associated with said sensor line for detecting a prescribed movement of the barrier from the closed position.

18. The system of claim 9 including a service housing located adjacent said mounted barrier containing a service loop of said at least one sensor line that must be extended to remove said barrier.

19. The system of claim 18 wherein said service loop is enclosed behind a door of said housing, and including a door opening sensor associated with said door whereby one of opening said door and severing said sensor line entering the service housing causes a fault signal to be detected in said sensor line and generated by said monitor system.

20. The system of claim 9 wherein said processor includes a plurality of predetermined fault levels corresponding to fault conditions including one of a break, bend, and movement of said tubular elements and/or said grate.

21. The system of claim 20 wherein said processor includes an initial baseline level which corresponds to the state of the sensor line in an undisturbed secure state, a plurality of threshold levels above or below said baseline level which correspond to the fault level, wherein said processor detects a current sensor signal reaching a threshold level.

22. The system of claim 21 wherein said processor determines said baseline level when the processor is turned on and is reset each time the processor turns off and on.

23. A security system for detecting an unauthorized activity and/or attempt to enter through an entrance of a secured area comprising:
a sensor line along which a sensor signal is transmitted;
an entrance barrier including a plurality of parallel tubular elements lying in a common plane, and said tubular elements being spaced wherein an intruder cannot enter between the tubular elements;
said tubular elements having hollow interiors and opposed open ends;
said sensor line being routed through said tubular elements;
a routing channel disposed adjacent open ends of said tubular elements, said sensor line passing through said routing channel to route said sensor line in and out of said tubular elements; and
a monitoring system comprising a signal for transmitting a sensor signal along said sensor line, a signal receiver for receiving said sensor signal, and a processor for processing said sensor signal to detect a predetermined deviation in said sensor signal representing one of a plurality of predetermined fault conditions;
whereby any predetermined deviation or severance of any of the tubular elements and sensor line is detected and a visual and/or audible notification may be produced for warning.

24. The system of claim 23 including a longitudinal reinforcing member encased within said tubular elements, said sensor line being laced through said tubular elements alongside said reinforcing members whereby a complete severance of said tubular element required for entry is delayed after severance of the sensor line and generation of a fault signal until said reinforcing member is cut through whereby guard personnel is provided sufficient time to arrive at the scene before intrusion.

25. The system of claim 23 wherein said first tubular elements and said second tubular elements include intersecting plastic pipe; and a cross-section fitting having four legs receiving the ends of the first tubular elements and ends of said second tubular elements at the intersection thereof.

26. The system of claim 25 wherein said plastic pipe include a filler material wherein said sensor line is embedded in said filler material.

27. The system of claim 23 including an encasement unit having first and second encasement sections being constructed and arranged to fit together and encase said tubular elements to protect the elements against accumulations of encrustations, barnacles, and the like when deployed under water whereby the encasement unit may be removed from the grid and replaced when needed while the grid remains protected.

28. The system of claim 23 including a first intrusion sensor for detecting one of a bending and severance of a tubular element representing a fault condition, a second intrusion sensor disposed relative to the barrier to detect an attempt to move the barrier signifying a fault condition, and generating a fault signal upon detecting one or more of the fault conditions.

29. The system of claim 28 including a service housing located adjacent said mounted barrier containing a service loop of sensor line that must be extended to remove said barrier, said service loop being enclosed behind a door of said housing, and said first intrusion sensor includes a door opening sensor whereby one of opening said door and severing said sensor line entering the housing causes a fault signal to be detected in said sensor line and a fault signal to be generated by said monitor system.

30. The system of claim 23 including structural transverse members traversing said tubular elements laterally to fix the same in place.

31. A security system for detecting an unauthorized activity and/or attempt to enter through an entrance of a secured area comprising:
an entrance barrier including a plastic grid of first tubular elements and second tubular elements made of a plastic material having hollow interiors and lying in a common plane;
a sensor line for transmitting a baseline sensor signal and a current sensor signal routed through said first and second signal lines;
a plurality of plastic cross-intersections formed by said first tubular elements and second tubular elements intersecting one another and forming a cross-through passage for crossing of said sensor line through said tubular elements;
said sensor line extending through said first tubular elements to cross over the sensor line extending through said second tubular elements at each said cross-passage; and
a monitoring system comprising a signal transmitter for transmitting said sensor signal along said sensor line, a signal receiver for receiving said sensor signal, and a processor for processing said current sensor signal to detect a deviation in said sensor signal representing a predetermined fault condition;
whereby any predetermined deviation or severance of any of the plastic tubular elements and sensor line is detected and a visual and/or audible notification may be produced for warning.

32. The system of claim 31 wherein said plastic pipes include a filler material wherein said sensor line is embedded in said filler material.

33. The system of claim 32 said filler material includes precision grout.

34. The system of claim 32 wherein said plastic pipe is PVC pipe.

35. The system of claim 31 wherein said processor includes a plurality of predetermined fault levels corresponding to fault conditions including one of a break, bend, and movement of said tubular elements and/or said grate.

36. The system of claim 35 wherein said processor includes an initial baseline level which corresponds to the state of the sensor line in an undisturbed secure state, a plurality of threshold levels above or below said baseline level which correspond to the fault level, wherein said processor detects a current sensor signal reaching a threshold level.

37. The system of claim 36 wherein said processor determines said baseline level when the processor is turned on and is reset each time the processor turns off and on.

\* \* \* \* \*